United States Patent
Koenigsdorfer et al.

(10) Patent No.: US 8,772,458 B2
(45) Date of Patent: Jul. 8, 2014

(54) CRYSTALLINE ANTI-HTNFALPHA ANTIBODIES

(71) Applicant: AbbVie Biotechnology Ltd, Hamilton (BM)

(72) Inventors: Anette Koenigsdorfer, Ilvesheim (DE); Stefan Gottschalk, Grunwald (DE); Hans-Juergen Krause, Biblis (DE); Gerhard Winter, Penzberg (DE); David W. Borhani, Hartsdale, NY (US); Wolfgang Fraunhofer, Newton, MA (US)

(73) Assignee: AbbVie Biotechnology Ltd, Hamilton (BM)

( * ) Notice: Subject to any disclaimer, the term of this patent is extended or adjusted under 35 U.S.C. 154(b) by 0 days.

(21) Appl. No.: 13/774,706

(22) Filed: Feb. 22, 2013

(65) Prior Publication Data

US 2013/0309309 A1   Nov. 21, 2013

Related U.S. Application Data

(60) Division of application No. 13/225,281, filed on Sep. 2, 2011, now Pat. No. 8,436,149, which is a continuation of application No. 11/977,677, filed on Oct. 25, 2007, now Pat. No. 8,034,906.

(60) Provisional application No. 60/855,104, filed on Oct. 27, 2006.

(51) Int. Cl.
C07K 16/00 (2006.01)

(52) U.S. Cl.
USPC .................................................. 530/388.15

(58) Field of Classification Search
None
See application file for complete search history.

(56) References Cited

U.S. PATENT DOCUMENTS

| | | | |
|---|---|---|---|
| 5,231,024 A | 7/1993 | Meoller et al. |
| 5,656,272 A | 8/1997 | Le |
| 6,090,382 A | 7/2000 | Salfeld et al. |
| 6,258,562 B1 | 7/2001 | Salfeld et al. |
| 6,448,380 B2 | 9/2002 | Rathjen |
| 6,451,983 B2 | 9/2002 | Rathjen |
| 6,498,237 B2 | 12/2002 | Rathjen |
| 6,509,015 B1 | 1/2003 | Salfeld et al. |
| 7,070,775 B2 | 7/2006 | Le |
| 7,192,584 B2 | 3/2007 | Le |
| 7,223,394 B2 | 5/2007 | Salfeld et al. |
| 7,250,165 B2 | 7/2007 | Heavner |
| 7,276,239 B2 | 10/2007 | Le |
| 7,541,031 B2 | 6/2009 | Salfeld et al. |
| 7,588,761 B2 | 9/2009 | Salfeld et al. |
| 7,863,426 B2 | 1/2011 | Wan et al. |
| 7,919,264 B2 | 4/2011 | Maksymowych et al. |
| 7,960,516 B2 | 6/2011 | Matheus et al. |
| 8,034,906 B2 | 10/2011 | Borhani et al. |
| 8,206,714 B2 | 6/2012 | Salfeld et al. |
| 8,372,401 B2 | 2/2013 | Salfeld et al. |
| 8,414,894 B2 | 4/2013 | Salfeld et al. |
| 8,436,149 B2 | 5/2013 | Borhani et al. |
| 2002/0136719 A1 | 9/2002 | Shenoy et al. |
| 2003/0012786 A1 | 1/2003 | Teoh et al. |
| 2003/0049725 A1 | 3/2003 | Heavner |
| 2003/0161828 A1 | 8/2003 | Abdelghany et al. |
| 2003/0206898 A1 | 11/2003 | Fischkoff et al. |
| 2003/0219438 A1 | 11/2003 | Salfeld et al. |
| 2003/0235585 A1 | 12/2003 | Fischkoff et al. |
| 2004/0009172 A1 | 1/2004 | Fischkoff et al. |
| 2004/0033228 A1 | 2/2004 | Krause et al. |
| 2004/0120952 A1 | 6/2004 | Knight |
| 2004/0126372 A1 | 7/2004 | Banerjee et al. |
| 2004/0126373 A1 | 7/2004 | Banerjee et al. |
| 2004/0131614 A1 | 7/2004 | Banerjee et al. |
| 2004/0136989 A1 | 7/2004 | Banerjee et al. |
| 2004/0136990 A1 | 7/2004 | Banerjee et al. |
| 2004/0136991 A1 | 7/2004 | Banerjee et al. |
| 2004/0151722 A1 | 8/2004 | Banerjee et al. |
| 2004/0166111 A1 | 8/2004 | Kaymakcalan et al. |
| 2004/0219142 A1 | 11/2004 | Banerjee et al. |
| 2005/0019794 A1 | 1/2005 | Nassef et al. |
| 2005/0123541 A1 | 6/2005 | Heavner |
| 2005/0249735 A1 | 11/2005 | Le |
| 2006/0009385 A1 | 1/2006 | Hoffman et al. |
| 2006/0018907 A1 | 1/2006 | Le |
| 2006/0083741 A1 | 4/2006 | Hoffman et al. |
| 2006/0153846 A1 | 7/2006 | Krause et al. |

(Continued)

FOREIGN PATENT DOCUMENTS

| | | |
|---|---|---|
| WO | WO-97/29131 A1 | 8/1997 |
| WO | WO-02/072636 A2 | 9/2002 |

(Continued)

OTHER PUBLICATIONS

Baldock, "A comparison of microbatch and vapour diffusion for initial screening of crystallization conditions," *Journal of Crystal Growth*, Oct. 1996, vol. 168, No. 1-4, pp. 170-174 (abstact only).

Data Sheet: Drum Rollers—Portable Drum Rotators Drum Mixers, URL<:http://web.archive.org/web/20070117013405/http://www.morsemfgeo.com/products/201-Portable-Drum-Roller.htm>., Jan. 2007 [retrieved on Dec. 2, 2008].

Data Sheet: Fisher Scientific Hematology/Chemistry Mixer Fisher Scientific, http://www.fishersci.com/, 2008 [Retrieved on Dec. 2, 2008].

Jen et al., "Diamonds in the Rough: Protein Crytsals from a Formulation Perspective," *Pharmaceutical Research*, 2001, vol. 18, No. 11, pp. 1483-1488.

(Continued)

*Primary Examiner* — Suzanne M Noakes
(74) *Attorney, Agent, or Firm* — McCarter & English, LLP; Cristin H. Cowles; Soo-Hwa Kim

(57) ABSTRACT

The present invention relates to a batch crystallization method for crystallizing an anti-hTNFalpha antibody which allows the production of said antibody on an industrial scale; antibody crystals as obtained according to said method; compositions containing said crystals as well as methods of use of said crystals and compositions.

21 Claims, 4 Drawing Sheets

(56) References Cited

U.S. PATENT DOCUMENTS

| | | |
|---|---|---|
| 2006/0246073 A1 | 11/2006 | Knight |
| 2007/0003548 A1 | 1/2007 | Heavner |
| 2007/0041905 A1 | 2/2007 | Hoffman et al. |
| 2007/0071747 A1 | 3/2007 | Hoffman et al. |
| 2007/0081996 A1 | 4/2007 | Hoffman et al. |
| 2007/0172897 A1 | 7/2007 | Maksymowych et al. |
| 2007/0196373 A1 | 8/2007 | Le |
| 2007/0202104 A1 | 8/2007 | Banerjee et al. |
| 2007/0292442 A1 | 12/2007 | Wan et al. |
| 2007/0298040 A1 | 12/2007 | Le |
| 2008/0025976 A1 | 1/2008 | Le |
| 2008/0118496 A1 | 5/2008 | Medich et al. |
| 2008/0131374 A1 | 6/2008 | Medich et al. |
| 2008/0166348 A1 | 7/2008 | Kupper et al. |
| 2008/0193466 A1 | 8/2008 | Banerjee et al. |
| 2008/0227136 A1 | 9/2008 | Pla et al. |
| 2008/0292642 A1 | 11/2008 | Borhani et al. |
| 2008/0311043 A1 | 12/2008 | Hoffman et al. |
| 2009/0017472 A1 | 1/2009 | Stuhlmuller et al. |
| 2009/0028794 A1 | 1/2009 | Medich et al. |
| 2009/0068172 A1 | 3/2009 | Kaymakcalan et al. |
| 2009/0110679 A1 | 4/2009 | Li et al. |
| 2009/0123378 A1 | 5/2009 | Wong et al. |
| 2009/0148513 A1 | 6/2009 | Fraunhofer et al. |
| 2009/0202557 A1 | 8/2009 | Argiriadi et al. |
| 2009/0226530 A1 | 9/2009 | Lassner et al. |
| 2009/0239259 A1 | 9/2009 | Hsieh |
| 2009/0258018 A1 | 10/2009 | Medich et al. |
| 2009/0271164 A1 | 10/2009 | Peng et al. |
| 2009/0280065 A1 | 11/2009 | Willian et al. |
| 2009/0291062 A1 | 11/2009 | Fraunhofer et al. |
| 2009/0304682 A1 | 12/2009 | Hoffman et al. |
| 2009/0317399 A1 | 12/2009 | Pollack et al. |
| 2010/0003243 A1 | 1/2010 | Okun et al. |
| 2010/0016557 A1 | 1/2010 | Salfeld et al. |
| 2010/0021451 A1 | 1/2010 | Wong |
| 2010/0040604 A1 | 2/2010 | Salfeld et al. |
| 2010/0040630 A1 | 2/2010 | Elden et al. |
| 2010/0160894 A1 | 6/2010 | Julian et al. |
| 2010/0278822 A1 | 11/2010 | Fraunhofer et al. |
| 2011/0002935 A1 | 1/2011 | Wan et al. |
| 2011/0054414 A1 | 3/2011 | Shang et al. |
| 2011/0171227 A1 | 7/2011 | Okun et al. |
| 2011/0300151 A1 | 12/2011 | Okun et al. |
| 2012/0014956 A1 | 1/2012 | Kupper et al. |
| 2012/0039900 A1 | 2/2012 | Stuhlmüller et al. |
| 2012/0077213 A1 | 3/2012 | Pla et al. |
| 2012/0107783 A1 | 5/2012 | Julian et al. |
| 2012/0129185 A1 | 5/2012 | Maksymowych et al. |
| 2012/0171123 A1 | 7/2012 | Medich et al. |
| 2012/0177596 A1 | 7/2012 | Fischkoff et al. |
| 2012/0258114 A1 | 10/2012 | Fischkoff et al. |
| 2012/0282262 A1 | 11/2012 | Okun et al. |
| 2012/0282270 A1 | 11/2012 | Krause et al. |
| 2013/0004507 A1 | 1/2013 | Fischkoff et al. |
| 2013/0028903 A1 | 1/2013 | Wan et al. |
| 2013/0115224 A1 | 5/2013 | Salfeld et al. |

FOREIGN PATENT DOCUMENTS

| | | |
|---|---|---|
| WO | WO-2004/009776 A2 | 1/2004 |
| WO | WO-02/12502 A9 | 3/2004 |
| WO | WO-2005121177 A2 | 12/2005 |
| WO | WO-2006012500 A9 | 2/2006 |
| WO | WO-2006069036 A2 | 6/2006 |
| WO | WO-2008/121301 A1 | 10/2008 |
| WO | WO-2009/020654 A1 | 2/2009 |

OTHER PUBLICATIONS

McPherson, "A comparison of salts for the crystallization of macromolecules," *Protein Science*, 2001, vol. 10, pp. 418-422.

Yang et al., "Crystalline Monoclonal Antibodies for Subcutaneous Delivery," *Proceedings of the National Academy of Sciences* Jun. 10, 2003. vol. 100, No. 12, pp. 6934-6939.

Baldock, "A comparison of microbatch and vapour diffusion for initial screening of crystallization conditions," *Journal of Crystal Growth*, Oct. 1996, vol. 168, No. 1-4, pp. 170-174.

Connell, G. E., et al., "A Human IgG Myeloma Protein Crystallizing with Rhombohedral Symmetry," Can. J. Biochem., 1973, vol. 51, pp. 1137-1141.

Harris, L. J., et al., "The Three-dimensional Structure of an Intact Monoclonal Antibody for Canine Lymphoma," Nature, 1992, vol. 360, pp. 369-372.

International Preliminary Report on Patentability for Application No. PCT/US08/04006, dated Aug. 28, 2009.

International Search Report for Application No. PCT/US09/000568, dated May 13, 2009.

International Search Report for Application No. PCT/U508/009549, dated Dec. 17, 2008.

International Search Report and Written Opinion for Application No. PCT/US08/04006, dated Jul. 2, 2008.

International Search Report for Application No. PCT/US07/022622, dated Sep. 4, 2008.

Jentoft, J. E., et al., "Characterization of a Human Cryoglobulin Complex: A Crystalline Adduct of a Monoclonal immunoglobulin G and Albumin," Biocehmistry, 1982, vol. 21, pp. 289-294.

Jones, H. B., "On a New Substance Occurring in the Urine of a Patient with Mollities Ossium," Phil. Tr. Royal Soc. London, 1848, vol. 138, pp. 55-62.

Mills, L. E., et al., "Crystallocryoglobulinemia Resulting from Human Monoclonal Antibodies to Albumin," Annals of Internal Medicine, 1983, vol. 99, pp. 601-604.

Nisonoff, A., et al. "Properties of Crystallized Rabbit Anti-p-Azobenzoate Antibody," Cold Spring Harb. Symp. Quant. Biol., 1967, vol. 32, pp. 89-93.

Putnam, F. W., "Abnormal Human Serum Globulins," 1955, Science, vol. 122, pp. 275-277.

Rajan, S. S., et al., "Three-Dimensional Structure of the Mcg IgG1 Immunoglobulin," 1983, Molecular Immunology, vol. 20, pp. 787-799.

Sarma, V. R., et al., "The Three-Dimensional Structure at 6 A Resolution of a Human γG1 Immunoglobulin Molecule," The Journal of Biological Chemistry, 1971, vol. 246, pp. 3753-3759.

Terry, W. D., et al., "Crystallographic Studies of a Human Immunoglobulin," Nature, 1968, vol. 220, pp. 239-241.

Von Bonsdorff, B., et al., "On the Presence of a High-molecular Crystallizable Protein in Blood Serum in Myeloma," Folia Haemat., 1938, vol. 59:, p. 184-208.

Weber, P.C., "Overview of Crystallization Methods," Methods in Enzymology, 1997, vol. 276, pp. 13-22.

Klyushnichenko, V., "Protein Crystallization: From HTS to Kilogram Scale," Curr. Opin. in Drug Discovery & Development, 6(6): 848-854, 2003.

McPherson, A., "Current Approaches to Macromolecular Crystallization" European Journal of Biochemistry, 1990, vol. 189, pp. 1-23.

Kundrot, C.E., "Which Strategy for a Protein Crystallization Project?" Cellular Molecular Life Science, 2004, vol. 61, pp. 525-536.

Benevenuti et al., "Crystallization of Soluble Proteins in Vapor Diffusion for X-ray Crystallography," Nature Protocols, published on-line Jun. 28, 2007, 2(7):1633-1651.

Cudney R., "Protein Crystallization and Dumb Luck," The Rigaku Journal, 1999, vol. 16, No. 1, pp. 1-7.

Drenth, "Principles of Protein X-Ray Crystallography", 2nd Edition, 1999, Springer-Verlag New York Inc., Chapter 1, p. 1-21.

Ahamed et al. "Phase Behaviour of Intact Monoclonal Antibody," Biochemical Journal, Jul. 2007, vol. 93, pp. 610-619.

CRYSTALLINE ANTI-HTNFALPHA ANTIBODIES

RELATED APPLICATIONS

This application is a divisional application of U.S. application Ser. No. 13/225,281, filed Sep. 2, 2011, which is a continuation application of U.S. application Ser. No. 11/977,677, filed Oct. 25, 2007, now U.S. Pat. No. 8,034,906, issued Oct. 11, 2011, which in turn claims priority to U.S. Provisional Application Ser. No. 60/855,104, filed Oct. 27, 2006. The entire contents of each of these applications are expressly incorporated herein by reference.

The present invention relates to a batch crystallization method for crystallizing an anti-hTNFalpha antibody which allows the production of said antibody on an industrial scale; antibody crystals as obtained according to said method; compositions containing said crystals as well as methods of use of said crystals and compositions.

TECHNICAL BACKGROUND a) Antibody Crystals

With over 100 monoclonal antibodies currently being evaluated in clinical study phases 2 or 3, the mAb market can be considered one of the most promising biopharmaceutical markets. As these drugs have to be delivered in single doses often exceeding 100 mg, there is an urgent need to find suitable formulation strategies satisfying stability, safety and patient compliance.

However, highly concentrated liquid mAb formulations show increased viscosity, hindering syringe ability through patient friendly thin needles. Furthermore, the aggregation tendency of mAb molecules at such high concentrations exponentially increases when compared to moderately concentrated solutions. This is unacceptable, in all means, regarding safety and stability requirements.

Thus, the delivery of high mAb doses is restrained to large volumes, which generally have to be delivered via infusion. This way of dosing is cost intensive and significantly reduces the patient's compliance.

Therefore, pharmaceutically applicable low volume mAb crystal suspensions for subcutaneous injection would be highly desirable. Theoretically, degradation pathways influencing the mAb integrity should be significantly decelerated due to the rigidity of a crystal lattice, where motions in the protein structure are hindered. Moreover, it can be expected that the increase in viscosity would be significantly reduced when comparing highly concentrated crystal suspensions with liquid formulations. With respect to sustained release, it might be possible to generate or alter protein crystals in that way that they dissolve slowly when brought into the patient's body. This would be a very elegant way to deliver a sustained release formulation, as the extensive use of excipients and processes harming the mAb structure would be prevented.

Despite the great potential in using protein crystals as drug substance, few attempts have been made to systematically evaluate this strategy.

A well-known exemption is insulin, which was successfully crystallized decades ago. Today, the use of crystal suspensions of insulin is well described, offering stable and long acting formulations being well established on the market. The discrepancy between the development of insulin crystals and crystallization of all other proteins might be related to the fact that ordered insulin aggregates are natively formed in the pancreas. Thus, insulin crystals are easily obtained when insulin is brought in contact with an excess of zinc ions. Most other proteins tend to form unordered precipitates rather than crystals, and therefore, finding crystallization conditions for a protein is a time consuming, non-trivial task.

Despite a great interest in harvesting protein crystals for x-ray diffraction analysis, the quest of finding suitable crystallization conditions still is an empirical science, as in principle any protein behaves differently. To date, no general rule has been found which might reliably predict by reason alone a successful crystallization condition for a protein of choice. Thus, obtaining crystals of a given protein always is referred to be the "bottle neck" of whatever intended application is planned later on.

To make things even more challenging, antibodies are described to be especially hard to crystallize, due to the flexibility of the molecule.

Nevertheless, examples of immunoglobulin crystals have been known for a long time. The first example of immunoglobulin crystals were described 150 years ago by an English physician, Henry Bence Jones; he isolated crystals of an abnormal Ig light chain dimer from the urine of a myeloma patient (Jones 1848). Such abnormal Igs have been known ever since as Bence Jones proteins. In 1938, the spontaneous crystallization of a distinct abnormal Ig from the serum of a myeloma patient was described (von Bonsdorf, Groth et al. 1938), apparently an Ig heavy chain oligomer (MW 200 kDa).

Crystalline human immunoglobulins of normal structure (two heavy chains linked to two light chains) were described over the next thirty years, again mostly isolated from myeloma patients (Putnam 1955). Davies and co-workers were the first to characterize the structure of an intact human myeloma antibody, named "Dob", using x-ray crystallography (Terry, Matthews et al. 1968), and they determined its three-dimensional structure in 1971 (Sarma, Silverton et al. 1971). Their pioneering work was followed by that of others, yielding the crystal structures of the IgG "Kol" (Huber, Deisenhofer et al. 1976), the IgG "Mcg" (Rajan, Ely et al. 1983), and a canine lymphoma IgG2a (Harris, Larson et al. 1992).

Crystals of immunoglobulins retain their distinctive immunological activities upon re-dissolution. Nisonoff et al. reported in 1968 on a rabbit anti-p-azobenzoate antibody, "X4", that was easily crystallized. Antibody X4 was extensively characterized before crystallization as well as after re-dissolution of the crystals. [$^{125}$I]-p-iodobenzoate was found to bind specifically and potently to re-dissolved X4; the re-dissolved crystals also exhibited multiple specific Ouchterlony immunodiffusion reactions typical of the unpurified rabbit serum (Nisonoff, Zappacosta et al. 1968). Connell and co-workers described a human myeloma gamma-immunoglobulin-1 kappa (IgG-κ), called "Tem", that crystallized spontaneously from serum at cold temperatures (Connell, Freedman et al. 1973). Tem crystals were found to be well-formed and possessed rhombohedral symmetry. Tem-containing serum was extensively characterized by agarose immunodiffusion techniques. Electrophoresis and immunodiffusion of a re-dissolved solution of the Tem crystals showed them to be identical with the material obtained from the serum by cryoprecipitation, and with the isolated myeloma protein (Connell, Freedman et al. 1973).

Mills and co-workers reported in 1983 an unusual crystallocryoglobulinemia resulting from human monoclonal antibodies to albumin (Mills, Brettman et al. 1983). Here, very similar cuboidal crystals were isolated from two patients. Redissolution of the crystals followed by electrophoresis and immunoelectrophoresis indicated that the crystals were composed of two protein components, a monoclonal IgG-lambda and human serum albumin in a 1:2 ratio (Jentoft, Dearborn et al. 1982). The components were separated on preparative scale by dissolution of the original crystals followed by column chromatography. Although neither separated component crystallized on its own, upon recombination the original bipartite complex reformed and then crystallized. Further study of the distinctive sedimentation characteristics and immunological reactivity of the redissolved, separated IgG and its Fab fragment with human serum albumin indicated that reassociation of the two redissolved, separated components was immunologic in nature, i.e. that the crystalline antibody once redissolved still possessed its native, highly specific (for human serum albumin) binding characteristics (Mills, Brettman et al. 1983).

Recently, Margolin and co-workers reported on the potential therapeutic uses of crystalline antibodies (Yang, Shenoy et al. 2003). They found that the therapeutic monoclonal antibody trastuzumab (Herceptin®) could be crystallized (Shenoy, Govardhan et al. 2002). Crystalline trastuzumab suspensions were therapeutically efficacious in a mouse tumor model, thus demonstrating retention of biological activity by crystalline trastuzumab (Yang, Shenoy et al. 2003).

b) Crystallization Techniques

Unlike some other scientific or engineering endeavors, the crystallization of diverse proteins cannot be carried out successfully using defined methods or algorithms. Certainly, there have been great technical advances in the last 20-30 years, as noted by the world-renowned expert in protein crystallization, A. McPherson. McPherson provides extensive details on tactics, strategies, reagents, and devices for the crystallization of macromolecules. He does not, however, provide a method to ensure that any given macromolecule can indeed be crystallized by a skilled person with reasonable expectation of success. McPherson states for example: "Whatever the procedure, no effort must be spared in refining and optimizing the parameters of the system, both solvent and solute, to encourage and promote specific bonding interactions between molecules and to stabilize them once they have formed. This latter aspect of the problem generally depends on the specific chemical and physical properties of the particular protein or nucleic acid being crystallized." (McPherson 1999, p. 159)

It is widely accepted by those skilled in the art of protein crystallization that no algorithm exists to take a new protein of interest, apply definite process steps, and thereby obtain the desired crystals.

Several screening systems a commercially available (for example Hampton 1 and 2, Wizzard I and II) which allow, on a microliter scale, to screen for potentially suitable crystallization conditions for a specific protein. However, positive results obtained in such a screening system do not necessarily allow successful crystallization in a larger, industrially applicable batch scale. Conversion of microliter-size crystallization trials into industrial dimensions is described to be a challenging task (see Jen et al., 2001).

Baldock et al (1996) reported on a comparison of microbatch and vapor diffusion for initial screening of crystallization conditions. Six commercially available proteins were screened using a set of crystallization solutions. The screens were performed using the most common vapor diffusion method and three variants of a microbatch crystallization method, including a novel evaporation technique. Out of 58 crystallization conditions identified, 43 (74%) were identified by microbatch, while 41 (71%) were identified by vapor diffusion. Twenty-six conditions were found by both methods, and 17 (29%) would have been missed if microbatch had not been used at all. This shows that the vapor diffusion technique, which is most commonly used in initial crystallization screens does not guarantee positive results.

c) hTNFalpha Antibody Crystals

Human TNFalpha (hTNFalpha) is considered as a causative agent of numerous diseases. There is, therefore, a great need for suitable methods of treating such hTNFalpha related disorders. One promising therapeutic approach comprises the administration of pharmaceutically effective doses of anti-human TNFalpha antibodies. Recently one such antibody, designated D2E7, or generically adalimumab, has been put on the market and is commercialised under the trade name HUMIRA®.

WO-A-02/072636 disclosed the crystallization of the whole, intact antibodies Rituximab, Infliximab and Trastuzumab. Most of the crystallization experiments were performed with chemicals with unclear toxicity, like imidazole, 2-cyclohexyl-ethanesulfonate (CHES), methylpentanediol, copper sulphate, and 2-morpholino-ethanesulfonate (MES). Most of the examples used seed crystals to initiate crystallization.

WO-A-2004/009776 disclosed crystallization experiments in the microliter scale using the sitting drop vapor diffusion technique by mixing equal volumes (1 µl) of different crystallization buffers and D2E7 F(ab)$'_2$ or Fab fragments. While several experimental conditions were reported for each of said fragments, no successful crystallization of the whole, intact D2E7 antibody was reported.

Methods for preparing crystals of any given anti-human TNFalpha whole antibodies, in particular of D2E7, therefore are not available.

The problem to be solved according to the present invention is, therefore, to develop suitable batch crystallization conditions for anti-hTNFalpha antibodies, in particular for the human anti-hTNFalpha antibody D2E7, and to establish crystallization process conditions applicable to volumes relevant for industrial antibody crystal production. At the same time a crystallization process should be established that does not make use of toxic agents, which might negatively affect the pharmaceutical applicability of such antibodies.

SUMMARY OF THE INVENTION

The above-mentioned problem was, surprisingly, solved by the finding that it is possible to obtain crystals of a whole anti-hTNFalpha antibody in batch crystallization volumes above the microliter scale by applying physiologically acceptable inorganic phosphate salts as the crystallization-inducing agent.

PREFERRED EMBODIMENTS

In a first aspect the invention relates to a batch crystallization method for crystallizing an anti-hTNFalpha antibody, comprising the steps of:

a) providing an aqueous solution of said antibody in admixture with an inorganic phosphate salt as crystallization agent, as for example by mixing an aqueous solution of said antibody, wherein the antibody preferably is present in dissolved form, with an aqueous crystallization solution comprising an inorganic phosphate salt as crystallization agent in dissolved form, or alternatively by adding said crystallization agent in solid form; and b) incubating said aqueous crystallization mixture until crystals of said antibody are formed.

The crystallization method of the invention generally is performed at a pH of said aqueous crystallization mixture in the range of about pH 3 to about 5, in particular about 3.5 to about 4.5, or about 3.7 to about 4.2.

Moreover, said aqueous crystallization mixture may contain at least one buffer. Said buffer may, in particular, comprise an acetate component as main component, especially an alkali metal salt, in particular, sodium acetate. Said salt is adjusted by addition of an acid, in particular acetic acid, to the required pH. In a preferred embodiment of the crystallization method, the buffer concentration (total acetate) in said aqueous crystallization mixture is 0 to about 0.5 M, or about 0.02 to about 0.5 M, as for example about 0.05 to about 0.3 M, or about 0.15 to about 0.2 M.

In a further particular embodiment of the crystallization method according to the invention, the phosphate salt used as the precipitating agent is selected from hydrogenphosphate salts, such as mono- or dihydrogenphosphate salts, in particular an ammonium salt or an alkali metal salt, for example a salt containing $Na^+$ or $K^+$ ions, or a mixture thereof comprising of at least two different salts. Suitable examples are: $NaH_2PO_4$, $Na_2HPO_4$, $KH_2PO_4$, $K_2HPO_4$, $NH_4H_2PO_4$, $(NH_4)_2HPO_4$, and mixtures thereof.

In particular, the phosphate salt concentration in the crystallization mixture is in the range of about 1 to about 6 M, for example a range of about 1.0 to about 4.0 M, or about 1.0 to about 3.0 M, or about 1.5 to about 2.8 M, or about 2.0 to about 2.6M.

In a preferred embodiment of the invention, protein solution and crystallization solution are combined in a ratio of about 1:1. Thus, molarities of the buffering agents/crystallization agents in the original crystallization solution are about double as high as in the crystallization mixture.

Typically, the crystallization method is performed in a batch volume in the range of about 1 ml to about 20000 l, or 1 ml to about 15000 l, or 1 ml to about 12000 l, or about 1 ml to about 10000 l, or 1 ml to about 6000 l, or 1 ml to about 3000 l, or 1 ml to about 1000 l, or 1 ml to about 100 l, as for example about 50 ml to about 8000 ml, or about 100 ml to about 5000 ml, or about 1000 ml to about 3000 ml; or about 1 l to about 1000 l; or about 10 l to about 500 l.

In addition, the crystallization method of the invention may be performed so that at least one of the following additional crystallization conditions is achieved:

a) incubation is performed for between about 1 hour to about 60 days, for example about 1 to about 30 days, or about 2 to 10 days;

b) incubation is performed at a temperature between about 0° C. and about 50° C., for example about 4° C. and about 37° C.;

c) the antibody concentration (i.e. protein concentration) in the crystallization mixture is in the range of about 1 to 200 mg/ml or 1 to 100 mg/ml, for example 1.5 to 20 mg/ml, in particular in the range of about 2 to 15 mg/ml, or 5 to 10 mg/ml. The protein concentration may be determined according to standard procedures for protein determination.

According to a particularly preferred method, crystallization is performed under the following conditions of the crystallization mixture:

Phosphate salt: $NaH_2PO_4$, 1.5 to 2.5 M
buffer: total acetate, 0 to 0.3 M
pH: 3.6 to 4.2
anti-hTNFalpha concentration: 3 to 10 mg/ml
Temperature: 18 to 24° C.
Batch volume: 1 to 100 l
Agitation: None
Duration: 4 to 15 days The crystallization mixtures as outlined above are usually obtained by adding a crystallization agent in solution or as solid to the protein solution. Both solutions may be, but do not have to be buffered. Crystallization agent molarity and buffer molarity in the original crystallization solution is usually higher than in the crystallization mixture as it is "diluted" with the protein solution.

In a further embodiment, the crystallization method of the invention may further comprise the step of drying the obtained crystals. Suitable drying methods comprise evaporative drying, spray drying, lyophilization, vacuum drying, fluid bed drying, spray freeze drying, near critical drying, supercritical drying, and nitrogen gas drying.

In a further embodiment, the crystallization method of the invention may further comprise the step of exchanging the crystallization mother liquor with a different buffer, e.g. a buffer containing polyethylene glycol (PEG) with a molar mass in the range of about 300 to 8000 Daltons or mixtures of PEGs, by centrifugation, diafiltration, ultrafiltration or other commonly used buffer exchange techniques.

The present invention also relates to a crystal of an anti-hTNFalpha antibody, obtainable by a crystallization method as defined above and in general to crystals of an anti-hTNFalpha antibody The crystals of the invention are typically characterized by a needle-like morphology with a maximum length l of about 2-500 μm or about 100-300 μm and an l/d ratio of about 3 to 30, but may also have other geometrical appearances Said crystal may be obtained from a polyclonal antibody or, preferably, a monoclonal antibody.

In particular, said antibody is selected from the group consisting of: non-chimeric or chimeric antibodies, humanized antibodies, non-glycosylated antibodies, human antibodies and mouse antibodies. In particular the antibody to be crystallized is a non-chimeric, human antibody optionally further processed for improving the antigen-binding.

Preferably, said crystals are obtained from an IgG antibody such as, for example, an IgG1, IgG2, IgG3 or IgG4 antibody. In particular, said antibody is a whole anti-human TNFalpha antibody of the group IgG1.

In a preferred embodiment, the crystals are prepared from an isolated human antibody, that dissociates from hTNFalpha with a Kd of $1\times10^{-8}$ M or less, more preferably $1\times10^{-9}$ M or less, and even more preferably $5\times10^{-10}$ M or less, and a $K_a$ rate constant of $1\times10^{-3}$ $s^{-1}$ or less, both determined by surface plasmon resonance, and neutralizes hTNFalpha cytotoxicity in a standard in vitro L929 assay with an $IC_{50}$ of $1\times10^{-7}$ M or less.

In particular, said crystals may be prepared from an isolated human antibody with the following characteristics: a) dissociates from human TNFalpha with a $k_{off}$ rate constant of $1\times10^{-3}$ $s^{-1}$ or less, as determined by surface plasmon resonance; b) has a light chain CDR3 domain comprising the amino acid sequence of SEQ ID NO: 3, or modified from SEQ ID NO: 3 by a single alanine substitution at position 1, 4, 5, 7 or 8, or by one to five conservative amino acid substitutions at positions 1, 3, 4, 6, 7, 8 and/or 9; c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11, or by one to five conservative amino acid substitutions at positions 2, 3, 4, 5, 6, 8, 9, 10, 11 and/or 12.

More preferably, the antibody, or antigen-binding portion thereof, dissociates from human TNFalpha with a $k_{off}$ of $5 \times 10^{-4}$ s$^{-1}$ or less. Even more preferably, the antibody, or antigen-binding portion thereof, dissociates from human TNFalpha with a $k_{off}$ of $1 \times 10^{-4}$ s$^{-1}$ or less.

In a particularly preferred embodiment, said crystals are prepared from an isolated human antibody with a light chain variable region (LCVR) comprising the amino acid sequence of SEQ ID NO: 1 and a heavy chain variable region (HCVR) comprising the amino acid sequence of SEQ ID NO: 2.

Most preferred are crystals prepared from the antibody D2E7, as disclosed in WO-A-97/29131 or a functional equivalent thereof. Said antibody is recombinantly produced in Chinese hamster ovary cells and comprises a heavy chain sequence according to SEQ ID NO:6 and a light chain sequence according to SEQ ID NO: 5.

In a further embodiment, the invention relates to a solid, liquid or semi-solid pharmaceutical composition comprising: (a) crystals of an anti-hTNFalpha antibody as defined in any one of the following embodiments: (1) crystal of an anti-hTNFalpha antibody, obtainable by a batch crystallization method for crystallizing an anti-hTNFalpha antibody, comprising the steps of: (i) providing an aqueous solution of said antibody in admixture with an inorganic phosphate salt as crystallization agent; and (ii) incubating said aqueous crystallization mixture until crystals of said antibody are formed: (2) a crystal of an anti-hTNFalpha antibody, with the proviso that said antibody is not INFLIXIMAB; (3) the crystal according to (1) having a needle-like morphology with a maximum length 1 of about 2-500 μm and an l/d ratio of about 3 to 30; (4) the crystal according to (2) having a needle-like morphology with a maximum length 1 of about 2-500 μm and an l/d ratio of about 3 to 30; (5) the crystal according to (1). wherein said antibody is a polyclonal antibody or a monoclonal antibody. (6) the crystal according to (5). wherein said antibody is selected from the group consisting of: chimeric antibodies, humanized antibodies, non-glycosylated antibodies, human antibodies and mouse antibodies: (7) the crystal according to (5). wherein said antibody is an IgG antibody: (8) the crystal according to (5). wherein said antibody is selected from the group consisting of: IgG1, IgG2, IgG3 and IgG4 antibodies; (9) the crystal according to (8). wherein said antibody is an anti-humanTNFalpha antibody of the group IgG1: (10) the crystal according to (9). prepared from an isolated human antibody, that dissociates from hTNFalpha with a Kd of $1 \times 10^{-8}$ M or less and a Ka rate constant of $1 \times 10^{-3}$ s$^{-1}$ or less, both determined by surface plasmon resonance, and neutralizes hTNFalpha cytotoxicity in a standard in vitro L929 assay with an IC50 of $1 \times 10^{-7}$ M or less, and (b) at least one pharmaceutically acceptable excipient stably maintaining the antibody crystals.

Another aspect of this invention relates to a solid, liquid or semi-solid pharmaceutical composition comprising: (a) crystals of an anti-hTNFalpha antibody as defined herein, and (b) at least one pharmaceutically acceptable excipient encapsulating or embedding said antibody crystals. The composition may further comprise (c) at least one pharmaceutically acceptable excipient stably maintaining the antibody crystals. Moreover, encapsulation and embedding may be implemented in conjunction.

In particular, said compositions may have an antibody crystal concentration higher than about 1 mg/ml, in particular about 200 mg/ml or more, for example about 200 to about 600 mg/ml, or about 300 to about 500 mg/ml.

Said excipients may comprise at least one polymeric, optionally biodegradable carrier or at least one oil or lipid carrier.

Said polymeric carrier may be a polymer selected from one or more of the group consisting of: poly(acrylic acid), poly(cyanoacrylates), poly(amino acids), poly(anhydrides), poly(depsipeptide), poly(esters), poly(lactic acid), poly(lactic-co-glycolic acid) or PLGA, poly(β-hydroxybutryate), poly(caprolactone), poly(dioxanone); poly(ethylene glycol), poly(hydroxypropyl) methacrylamide, poly(organo) phosphazene, poly(ortho esters), poly(vinyl alcohol), poly(vinylpyrrolidone), maleic anhydride alkyl vinyl ether copolymers, pluronic polyols, albumin, alginate, cellulose and cellulose derivatives, collagen, fibrin, gelatin, hyaluronic acid, oligosaccharides, glycaminoglycans, sulfated polysaccharides, blends and copolymers thereof.

Said oil (or oily liquid) may be an oil (or oily liquid) selected from one or more of the group consisting of: oleaginous almond oil, corn oil, cottonseed oil, ethyl oleate, isopropyl myristate, isopropyl palmitate, mineral oil, light mineral oil, octyldodecanol, olive oil, peanut oil, persic oil, sesame oil, soybean oil, squalane, liquid triglycerides, liquid waxes, higher alcohols.

Said lipid carrier may be a lipid selected from one or more of the group consisting of: fatty acids and salts of fatty acids, fatty alcohols, fatty amines, mono-, di-, and triglycerides of fatty acids, phospholipids, glycolipids, sterols and waxes and related similar substances. Waxes are further classified in natural and synthetic products. Natural materials include waxes obtained from vegetable, animal or minerals sources such as beeswax, carnauba or montanwax. Chlorinated naphthalenes and ethylenic polymers are examples for synthetic wax products.

In a preferred embodiment, said composition is an injectable composition comprising anti-hTNFalpha antibody crystals as defined above and having an antibody crystal concentration in the range of about 10 to about 400 or about 50 to about 300 mg/ml.

In a further aspect the invention relates to a crystal slurry comprising anti-hTNFalpha antibody crystals as defined above having an antibody crystal concentration higher than about 100 mg/ml, for example about 150 to about 600 mg/ml, or about 200 to about 400 mg/ml.

The present invention also relates to a method for treating a mammal comprising the step of administering to the mammal an effective amount of whole anti-hTNFalpha antibody crystals as defined above or an effective amount of the composition as defined above. Preferably, said composition is administered by parenteral route, oral route, or by injection.

Furthermore, the present invention relates to a method of treating a hTNFalpha-related disorder in a subject that comprises administering a therapeutically effective amount of antibody crystals as defined above.

In particular, said hTNFalpha-related disorder is selected from:

an autoimmune disease, in particular rheumatoid arthritis, rheumatoid spondylitis, osteoarthritis and gouty arthritis, an allergy, multiple sclerosis, autoimmune diabetes, autoimmune uveitis and nephrotic syndrome; an infectious disease, transplant rejection or graft-versus-host disease, malignancy, pulmonary disorder, intestinal disorder, cardiac disorder, inflammatory bone disorders, bone resorption disease, alcoholic hepatitis, viral hepatitis, fulminant hepatitis, coagulation disturbances, burns, reperfusion injury, keloid formation, scar tissue formation, pyrexia, periodontal disease, obesity and radiation toxicity; a spondyloarthropathy, a pulmonary disorder, a coronary disorder, a metabolic disorder, anemia, pain, a hepatic disorder, a skin disorder, a nail disorder, or vasculitis, Behcet's disease, ankylosing spondylitis, asthma, chronic obstructive pulmonary disease (COPD), idiopathic pulmonary fibrosis (IPF), restenosis, diabetes, anemia, pain, a Crohn's disease-related disorder, juvenile rheumatoid arthritis (JRA), a hepatitis C virus infection, psoriasis, psoriatic arthritis, chronic plaque psoriasis, age-related cachexia, Alzheimer's disease, brain edema, inflammatory brain injury, chronic fatigue syndrome, dermatomyositis, drug reactions, edema in and/or around the spinal cord, familial periodic fevers, Felty's syndrome, fibrosis, glomerulonephritides (e.g. post-streptococcal glomerulonephritis or IgA nephropathy), loosening of prostheses, microscopic polyangiitis, mixed connective tissue disorder, multiple myeloma, cancer and cachexia, multiple organ disorder, myelo dysplastic syndrome, orchitism osteolysis, pancreatitis, including acute, chronic, and pancreatic abscess, periodontal disease polymyositis, progressive renal failure, pseudogout, pyoderma gangrenosum, relapsing polychondritis, rheumatic heart disease, sarcoidosis, sclerosing cholangitis, stroke, thoracoabdominal aortic aneurysm repair (TAAA), TNF receptor associated periodic syndrome (TRAPS), symptoms related to Yellow Fever vaccination, inflammatory diseases associated with the ear, chronic ear inflammation, or pediatric ear inflammation, uveitis, sciatica, prostatitis, endometriosis, choroidal neovascularization, lupus, Sjogren's syndrome, and wet macular degeneration.

Moreover, the present invention relates to the use of whole anti-hTNFalpha antibody crystals as defined above for preparing a pharmaceutical composition for treating a hTNFalpha-related disease as defined above.

Finally, the present invention provides anti-hTNFalpha antibody crystals as defined above for use in medicine.

DESCRIPTION OF FIGURES

FIG. 5: D2E7 crystals manufactured according to the invention and birefringence thereof.

DETAILED DESCRIPTION OF THE INVENTION

A. Definitions

Figure 1:
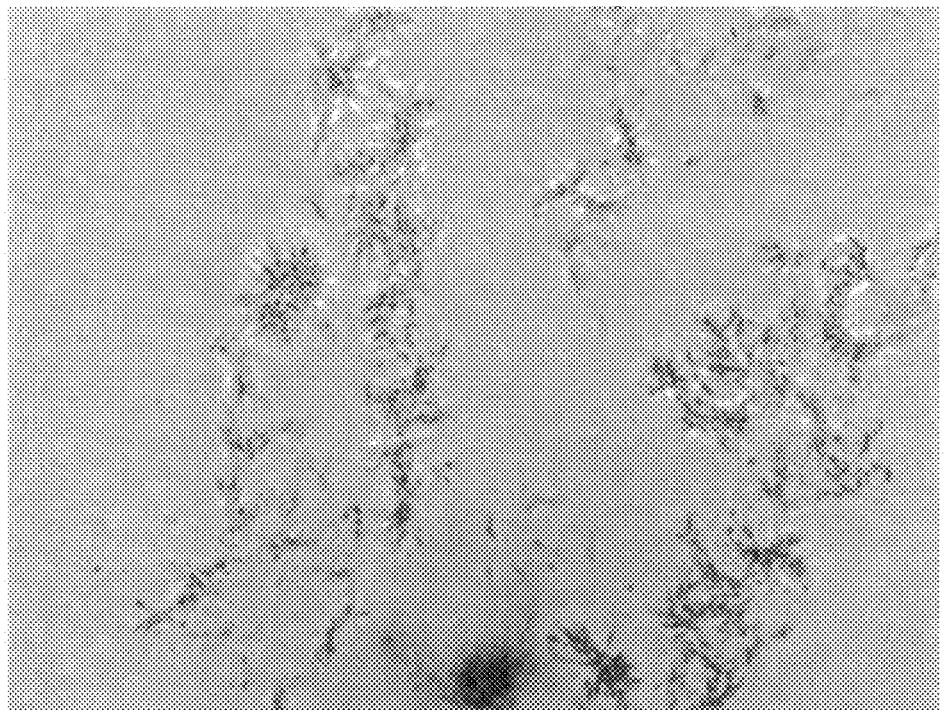
FIG. 1: D2E7 crystals from Example 37 after 6 days.

A "batch method of crystallization" comprises the step of adding the crystallization solution comprising the crystallization agent, preferably in dissolved form, to the solution of the antibody to be crystallized.

A "micro scale crystallization method", which may for example be based upon vapor diffusion, comprises the steps of admixing a small volume of antibody solution in the microliter range with a reservoir buffer containing a crystallization agent; placing a droplet of said mixture in a sealed container adjacent to an aliquot of said reservoir buffer; allowing exchange of solvent between the droplet and the reservoir by vapor diffusion, during which the solvent content in said droplet changes and crystallization may be observed if suitable crystallization conditions are reached.

A "crystallization agent", in the present case a phosphate salt, favors crystal formation of the antibody to be crystallized.

A "crystallization solution" contains said crystallization agent in dissolved form. Preferably said solution is an aqueous system, i.e. the liquid constituents thereof predominantly, consist of water. As for example, 80 to 100 wt.-% or 95 to 100 wt.-% or 98 to 100 wt.-% may be water.

Antibody "crystals" are one form of the solid state of matter of said protein, which is distinct from a second solid form, i.e. the amorphous state, which exists essentially as an unorganized, heterogeneous solid. Crystals have a regular three-dimensional structure, typically referred to as a lattice. An antibody crystal comprises a regular three-dimensional array of antibody molecules. See Giege, R. and Ducruix, A. Barrett, Crystallization of Nucleic Acids and Proteins, a Practical Approach, 2nd ed., pp. 1-16, Oxford University Press, New York (1999).

A "whole" or "intact" anti-hTNFalpha antibody as crystallized according to this invention, is a functional antibody that is able to recognize and bind to its antigen human TNFalpha in vitro and/or in vivo. The antibody may initiate subsequent immune system reactions of a patient associated with antibody-binding to its antigen, in particular Direct Cytotoxicity, Complement-Dependent Cytotoxicity (CDC), and Antibody-Dependent Cytotoxicity (ADCC). The antibody molecule has a structure composed of two identical heavy chains (MW each about 50 kDa) covalently bound to each other, and two identical light chains (MW each about 25 kDa), each covalently bound to one of the heavy chains. The four chains are arranged in a classic "Y" motif. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The complete antibody molecule has two antigen binding sites, i.e. is "bivalent". The two antigen binding sites are specific for one hTNFalpha antigen, i.e. the antibody is "mono-specific".

"Monoclonal antibodies" are antibodies that are derived from a single clone of B lymphocytes (B cells), and recognize the same antigenic determinant. Whole monoclonal antibodies are those that have the above-mentioned classic molecular structure that includes two complete heavy chains and two complete light chains. Monoclonal antibodies are routinely produced by fusing the antibody-producing B cell with an immortal myeloma cell to generate B cell hybridomas, which continually produce monoclonal antibodies in cell culture. Other production methods are available, as for example expression of monoclonal antibodies in bacterial, yeast, insect, or mammalian cell culture using phage-display technology; in vivo production in genetically modified animals, such as cows, goats, pigs, rabbits, chickens, or in transgenic mice which have been modified to contain and express the entire human B cell genome; or production in genetically modified plants, such as tobacco and corn. Anti-hTNFalpha antibodies from all such sources may be crystallized according to this invention.

The monoclonal antibodies to be crystallized according to the invention include "chimeric" anti-hTNFalpha antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass. As an example there may be mentioned a mouse/human chimera containing variable antigen-binding portions of a murine antibody and constant portions derived from a human antibody.

"Humanized" forms of non-human (e.g. murine) anti-hTNFalpha antibodies are also encompassed. These are chimeric antibodies that contain minimal sequence derived from a non-human immunoglobulin. For the most part, humanized antibodies are human immunoglobulins in which residues from a complementarity determining region (CDR) or hypervariable loop (HVL) of the human immunoglobulin are replaced by residues from a CDR or HVL of a non-human species, such as mouse, rat, rabbit or non-human primate, having the desired functionality. Framework region (FR) residues of the human immunoglobulin may replaced by corresponding non-human residues to improve antigen binding affinity. Furthermore, humanized antibodies may comprise residues that are found neither in the corresponding human or non-human antibody portions. These modifications may be necessary to further improve antibody efficacy.

A "human antibody" or "fully human antibody" is one, which has an amino acid sequence which corresponds to that of an antibody produced by a human or which is recombinantly produced. The term "human antibody", as used herein, is intended to include antibodies having variable and constant regions derived from human germline immunoglobulin sequences. The human antibodies of the invention may include amino acid residues not encoded by human germline immunoglobulin sequences (e.g. mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g. a mouse) that is transgenic for human immunoglobulin genes (see e.g. Taylor, L. D., et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

A "neutralizing antibody", as used herein (or an "antibody that neutralized hTNFalpha ☐activity"), is intended to refer to an antibody whose binding to hTNFalpha results in inhibition of the biological activity of hTNFalpha. This inhibition of the biological activity of hTNFalpha can be assessed by measuring one or more indicators of hTNFalpha biological activity, such as hTNFalpha-induced cytotoxicity (either in vitro or in vivo), hTNFalpha-induced cellular activation and hTNFalpha binding to hTNFalpha receptors. These indicators of hTNFalpha biological activity can be assessed by one or more of several standard in vitro or in vivo assays known in the art. Preferably, the ability of an antibody to neutralize hTNFalpha activity is assessed by inhibition of hTNFalpha-induced cytotoxicity of L929 cells. As an additional or alternative parameter of hTNFalpha activity, the ability of an antibody to inhibit hTNFalpha-induced expression of ELAM-1 on HUVEC, as a measure of hTNFalpha-induced cellular activation, can be assessed.

An "affinity matured" anti-hTNFalpha antibody is one with one or more alterations in one or more hypervariable regions, which result in an improvement in the affinity of the antibody for antigen, compared to a parent antibody. Affinity matured antibodies will have nanomolar or even picomolar affinities values for the target antigen. Affinity matured antibodies are produced by procedures known in the art. Marks et al., Bio/Technology 10:779-783 (1992) describes affinity maturation by VH and VL domain shuffling. Random mutagenesis of CDR and/or framework residues is described by: Barbas et al., Proc. Nat. Acad. Sci. USA 91:3809-3813 (1994); Scier et al., Gene 169:147-155 (1995); Yelton et al., J. Immunol. 155:1994-2004 (1995); Jackson et al., J. Immunol. 154(7):3310-9 (1995); and Hawkins et al., J. Mol. Biol. 226: 889-896 (1992).

An "isolated antibody", as used herein, is intended to refer to an antibody that is substantially free of other antibodies having different antigenic specificities (e.g. an isolated antibody that specifically binds hTNFalpha is substantially free of antibodies that specifically_bind antigens other than hTNFalpha). An isolated antibody that specifically binds hTNFalpha may, however, have cross-reactivity to other antigens, such as hTNFalpha molecules from other species. Moreover, an isolated antibody may be substantially free of other cellular material and/or chemicals.

The term "human TNFalpha" (abbreviated herein as hTNFalpha, or simply hTNF), as used herein, is intended to refer to a human cytokine that exists as a 17 kDa secreted form and a 26 kDa membrane-associated form, the biologically active form of which is composed of a trimer of noncovalently bound molecules. The structure of hTNFalpha is described further in, for example, Pennica, D., et al. (1984) Nature 312:724-729; Davis, J. M., et al. (1987) Biochemistry 26:1322-1326; and Jones, E. Y., et al. (1989) Nature 338:225-228. The term human TNFalpha is intended to include recombinant human TNFalpha (rhTNFalpha), which can be prepared by standard recombinant expression methods or purchased commercially (R & D Systems, Catalog No. 210-TA, Minneapolis, Minn.).

The term "$k_{off}$", as used herein, is intended to refer to the off rate constant for dissociation of an antibody from the antibody/antigen complex.

The term "$K_d$", as used herein, is intended to refer to the dissociation constant of a particular antibody-antigen interaction.

A "functional equivalent" of a specific "parent" anti-hTNFalpha antibody as crystallized according to the invention is one which shows the same antigen-specificity, differs however with respect to the molecular composition of the "parent" antibody on the amino acid level or glycosylation level. Said differences, however, may be merely such that the crystallization conditions do not deviate from the parameter ranges as disclosed herein.

"Encapsulation" of antibody crystals refers to a formulation where the incorporated crystals are individually coated by at least one layer of a coating material. In a preferred embodiment, such coated crystals may have a sustained dissolution rate.

"Embedding" of antibody crystals refers to a formulation where the crystals, which might be encapsulated or not, are incorporated into a solid, liquid or semi-solid carrier in a disperse manner. Such embedded crystallized antibody molecules may be released or dissolved in a controlled, sustained manner from the carrier.

B. Method of Crystallization

The crystallization method of the invention is in principle applicable to any anti-hTNFalpha antibody. Said antibody may be a polyclonal antibody or, preferably, a monoclonal antibody. Said antibody may be chimeric antibodies, humanized antibodies, human antibodies or non-human, as for example mouse antibodies, each in glycosylated or non-glycosylated form. In particular the method is applicable to D2E7 and functional equivalents thereof.

Preferably said anti-hTNFalpha antibody is an IgG antibody, in particular an anti human TNFalpha antibody of the group IgG1.

Unless otherwise stated the crystallization method of the invention makes use of technical equipment, chemicals and methodologies well known in the art. However, as explained above, the present invention is based on the surprising finding that the selection of specific crystallization conditions, in particular, the selection of specific crystallization agents, optionally further combined with specific pH conditions and/or concentration ranges of the corresponding agents (buffer, antibody, crystallization agent), allows for the first time to prepare reproducibly and in a large scale stable crystals of antibodies, in particular non-chimeric, human antibodies, directed against hTNF alpha, which can be further processed to form an active ingredient of a superior, highly advantageous pharmaceutical composition.

The starting material for performing the crystallization method normally comprises a concentrated solution of the antibody to be crystallized. The protein concentration may, for example, be in the range of about 5 to 75 mg/ml. Said solution may contain additives stabilizing said dissolved antibody, and it may be advisable to remove said additives in advance. This can be achieved by performing a buffer exchange step.

Preferably said starting material for performing the crystallization contains the antibody in an aqueous solution, having a pH adjusted in the range of about 3.2 to 8.2, or about 4.0 to 8.0, in particular about 4.5 to 6.5, preferably around 5.0 to 5.5. The pH may be adjusted by means of a suitable buffer applied in a final concentration of about 1 to 50 mM, in particular about 1 to 10 mM. The solution may contain additives, as for example in a proportion of about 0.01 to 15, or 0.1 to 5, or 0.1 to 2 wt.-% based on the total weight of the solution, like salts, sugars, sugar alcohols and surfactants, in order to further stabilize the solution. The excipients should preferably be selected from physiologically acceptable compounds, routinely applied in pharmaceutical preparations. As non-limiting examples there may be mentioned salts, like NaCl; surfactants, like polysorbate 80 (Tween 80), polysorbate 20 (Tween 20); sugars, like sucrose, trehalose; sugar alcohols, like mannitol, sorbitol; and buffer agents, like phosphate-based buffer systems, as sodium and potassium hydrogen phosphate buffers as defined above, acetate buffer, phosphate buffer, citrate buffer, TRIS buffer, maleate buffer or succinate buffer, histidine buffer; amino acids, like histidine, arginine and glycine.

The buffer exchange may be performed by means of routine methods, for example dialysis or ultrafiltration.

The initial protein concentration of the aqueous solution used as starting material should be in the range of about 0.5 to about 200 or about 1 to about 50 mg/ml.

Depending on the intended final batch size (which may be in the range of 1 ml to 20000 (twenty thousand) liters) an initial volume of said aqueous antibody solution is placed in an appropriate container (as for example a vessel, bottle or tank) made of inert material, as for example glass, polymer or metal. The initial volume of said aqueous solution may correspond to about 30 to 80%, normally about 50% of the final batch size.

If necessary the solution after having been filled into said container will be brought to standardized conditions. In particular, the temperature will be adjusted in the range of about 4° C. and about 37° C.

Then the crystallization solution, containing the crystallization agent in an appropriate concentration, optionally preconditioned in the same way as the antibody solution, is added to the antibody solution.

The addition of the crystallization solution is performed continuously or discontinuously optionally under gentle agitation in order to facilitate mixing of the two liquids. Preferably the addition is performed under conditions where the protein solution is provided under agitation and the crystallization solution (or agents in its solid from) is/are added in a controlled manner.

The formation of the antibody crystals is initiated by applying a phosphate salt, in particular a hydrogen phosphate salt, and preferably an alkali metal salt, or a mixture of at least two different alkali metal salts as defined above as the crystallization agent. The crystallization solution contains the agent in a concentration which is sufficient to afford a final concentration of the phosphate salt in said crystallization mixture in the range of about 1 to 6 M.

Preferably, the crystallization solution additionally contains an acidic buffer, i.e. different from that of the antibody solution, in a concentration suitable to allow the adjustment of the pH of the crystallization mixture in the range of about 3 to 5.

After having finished the addition of said crystallization solution, the thus obtained mixture may be further incubated for about 1 hour to about 60 days in order to obtain a maximum yield of antibody crystals. If appropriate, the mixture may, for example, be agitated, gently stirred, rolled or moved in a manner known per se.

Finally, the crystals obtained may be separated by known methods, for example filtration or centrifugation, as for example by centrifugation at about 200-20000 rpm, preferably 500-2000 rpm, at room temperature or 4° C. The remaining mother liquor may be discarded or further processed.

If necessary, the thus isolated crystals may be washed and subsequently dried, or the mother liquor can be exchanged by a different solvent system suitable for storage and/or final use of the antibodies suspended therein.

Antibody crystals formed according to the present invention may vary in their shape. Shapes typically may include needles, cone-like, spherical and sea urchin like shapes. The size of the crystals can be on the order of higher nm to mm size (as for example length). In some embodiments, the crystals are at least about 10 μm in size, and may be visible to the naked eye. For therapeutic administration, the size of the crystals will vary depending on the route of administration, for example, for subcutaneous administration the size of the crystals may be larger than for intravenous administration.

The shape of the crystals may be altered by adding specific additional additives to the crystallization mixture, as has been previously described for both protein crystals and crystals of low molecular weight organic and inorganic molecules.

If necessary, it may be verified that the crystals are in fact crystals of said antibody. Crystals of an antibody can be analyzed microscopically for birefringence. In general, crystals, unless of cubic internal symmetry, will rotate the plane of polarization of polarized light. In yet another method, crystals can be isolated, washed, resolubilized and analyzed by SDS-PAGE and, optionally, stained with an anti-Fc receptor antibody. Optionally, the resolubilized antibody can also be tested for binding to its hTNFalpha utilizing standard assays.

Crystals as obtained according to the invention may also be crosslinked to one another. Such crosslinking may enhance stability of the crystals. Methods for crosslinking crystals described, for example, in U.S. Pat. No. 5,849,296. Crystals can be crosslinked using a bifunctional reagent such as glutaraldehyde. Once crosslinked, crystals can be lyophilized and stored for use, for example, in diagnostic or therapeutic applications.

In some cases, it may be desirable to dry the crystal. Crystals may be dried by means of inert gases, like nitrogen gas, vacuum oven drying, lyophilization, evaporation, tray drying, fluid bed drying, spray drying, vacuum drying or roller drying. Suitable methods are well known.

Crystals formed according to the invention can be maintained in the original crystallization solution, or they can be washed and combined with other substances, like inert carriers or ingredients to form compositions or formulations comprising crystals of the invention. Such compositions or formulations can be used, for example, in therapeutic and diagnostic applications.

A preferred embodiment is to combine a suitable carrier or ingredient with crystals of the invention in that way that crystals of the formulation are embedded or encapsulated by an excipient. Suitable carriers may be taken from the non limiting group of: poly(acrylic acid), poly(cyanoacrylates), poly(amino acids), poly(anhydrides), poly(depsipeptide), poly(esters), poly(lactic acid), poly(lactic-co-glycolic acid) or PLGA, poly(β-hydroxybutryate), poly(caprolactone), poly(dioxanone); poly(ethylene glycol), poly(hydroxypropyl) methacrylamide, poly(organo) phosphazene, poly(ortho esters), poly(vinyl alcohol), poly(vinylpyrrolidone), maleic anhydride alkyl vinyl ether copolymers, pluronic polyols, albumin, alginate, cellulose and cellulose derivatives, collagen, fibrin, gelatin, hyaluronic acid, oligosaccharides, glycaminoglycans, sulfated polysaccharides, blends and copolymers thereof, SAIB, fatty acids and salts of fatty acids, fatty alcohols, fatty amines, mono-, di-, and triglycerides of fatty acids, phospholipids, glycolipids, sterols and waxes and related similar substances. Waxes are further classified in natural and synthetic products. Natural materials include waxes obtained from vegetable, animal or minerals sources such as beeswax, carnauba or montanwax. Chlorinated naphthalenes and ethylenic polymers are examples for synthetic wax products.

C. Compositions

Another aspect of the invention relates to compositions/formulations comprising anti-hTNFalpha antibody crystals in combination with at least one carrier/excipient.

The formulations may be solid, semisolid or liquid.

Formulations of the invention are prepared, in a form suitable for storage and/or for use, by mixing the antibody having the necessary degree of purity with a physiologically acceptable additive, like carrier, excipient and/or stabilizer (see for example Remington's Pharmaceutical Sciences, 16th Edn., Osol, A. Ed. (1980)), in the form of suspensions, lyophilized or dried in another way. Optionally further active ingredients, as for example different antibodies, biomolecules, chemically or enzymatically synthesized low-molecular weight molecules may be incorporated as well.

Acceptable additives are non-toxic to recipients at the dosages and concentrations employed. Nonlimiting examples thereof include:

Acidifying agents, like acetic acid, citric acid, fumaric acid, hydrochloric acid, malic acid, nitric acid, phosphoric acid, diluted phosphoric acid, sulfuric acid, tartaric acid.

Aerosol propellants, like butane, dichlorodifluoromethane, dichlorotetrafluoroethane, isobutane, propane, trichloromonofluoromethane.

Air displacements, like carbon dioxide, nitrogen;

Alcohol denaturants, like methyl isobutyl ketone, sucrose octacetate;

Alkalizing agents, like ammonia solution, ammonium carbonate, diethanolamine, diisopropanolamine, potassium hydroxide, sodium bicarbonate, sodium borate, sodium carbonate, sodium hydroxide, trolamine;

Antifoaming agents, like dimethicone, simethicone.

Antimicrobial preservatives, like benzalkonium chloride, benzalkonium chloride solution, benzelthonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, thymol.

Antioxidants, like ascorbic acid, acorbyl palmitate, butylated hydroxyanisole, butylated hydroxytoluene, hypophosphorous acid, monothioglycerol, propyl gallate, sodium formaldehyde sulfoxylate, sodium metabisulfite, sodium thiosulfate, sulfur dioxide, tocopherol, tocopherols excipient;

Buffering agents, like acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate, histidine.

Chelating agents, like edetate disodium, ethylenediaminetetraacetic acid and salts, edetic acid;

Coating agents, like sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyethylene glycol, polyvinyl acetate phthalate, shellac, sucrose, titanium dioxide, carnauba wax, microcystalline wax, zein, poly amino acids, other polymers like PLGA etc., and SAIB.

Coloring agent, like ferric oxide.

Complexing agents, like ethylenediaminetetraacetic acid and salts (EDTA), edetic acid, gentisic acid ethanolamide, oxyquinoline sulfate.

Desiccants, like calcium chloride, calcium sulfate, silicon dioxide.

Emulsifying and/or solubilizing agents, like acacia, cholesterol, diethanolamine (adjunct), glyceryl monostearate, lanolin alcohols, lecithin, mono- and di-glycerides, monoethanolamine (adjunct), oleic acid (adjunct), oleyl alcohol (stabilizer), poloxamer, polyoxyethylene 50 stearate, polyoxyl 35 caster oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, soritan monooleate, sorbitan monopalmitate, sorbitan monostearate, stearic acid, trolamine, emulsifying wax.

Filtering aids, like powdered cellulose, purified siliceous earth.

Flavors and perfumes, like anethole, benzaldehyde, ethyl vanillin, menthol, methyl salicylate, monosodium glutamate, orange flower oil, peppermint, peppermint oil, peppermint spirit, rose oil, stronger rose water, thymol, tolu balsam tincture, vanilla, vanilla tincture, vanillin.

Glidant and/or anticaking agents, like calcium silicate, magnesium silicate, colloidal silicon dioxide, talc.

Humectants, like glycerin, hexylene glycol, propylene glycol, sorbitol;

Ointment bases, like lanolin, anhydrous lanolin, hydrophilic ointment, white ointment, yellow ointment, polyethylene glycol ointment, petrolatum, hydrophilic petrolatum, white petrolatum, rose water ointment, squalane.

Plasticizers, like castor oil, lanolin, mineral oil, petrolatum, benzyl benzyl formate, chlorobutanol, diethyl pthalate, sorbitol, diacetylated monoglycerides, diethyl phthalate, glycerin, glycerol, mono- and di-acetylated monoglycerides, polyethylene glycol, propylene glycol, triacetin, triethyl citrate, ethanol.

Polypeptides, like low molecular weight (less than about 10 residues); Proteins, such as serum albumin, gelatin, or immunoglobulins;

Polymer membranes, like cellulose acetate membranes.

Solvents, like acetone, alcohol, diluted alcohol, amylene hydrate, benzyl benzoate, butyl alcohol, carbon tetrachloride, chloroform, corn oil, cottonseed oil, ethyl acetate, glycerin, hexylene glycol, isopropyl alcohol, methyl alcohol, methylene chloride, methyl isobutyl ketone, mineral oil, peanut oil, polyethylene glycol, propylene carbonate, propylene glycol, sesame oil, water for injection, sterile water for injection, sterile water for irrigation, purified water, liquid triglycerides, liquid waxes, higher alcohols.

Sorbents, like powdered cellulose, charcoal, purified siliceous earth, Carbon dioxide sorbents, barium hydroxide lime, soda lime.

Stiffening agents, like hydrogenated castor oil, cetostearyl alcohol, cetyl alcohol, cetyl esters wax, hard fat, paraffin, polyethylene excipient, stearyl alcohol, emulsifying wax, white wax, yellow wax.

Suppository bases, like cocoa butter, hard fat, polyethylene glycol;

Suspending and/or viscosity-increasing agents, like acacia, agar, alginic acid, aluminum monostearate, bentonite, purified bentonite, magma bentonite, carbomer 934p, carboxymethylcellulose calcium, carboxymethylcellulose sodium, carboxymethycellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, colloidal silicon dioxide, sodium alginate, tragacanth, xanthan gum;

Sweetening agents, like aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup;

Tablet binders, like acacia, alginic acid, sodium carboxymethylcellulose, microcrystalline cellulose, dextrin, ethylcellulose, gelatin, liquid glucose, guar gum, hydroxypropyl methylcellulose, methylcellulose, polyethylene oxide, povidone, pregelatinized starch, syrup.

Tablet and/or capsule diluents, like calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar, confectioner's sugar;

Tablet disintegrants, like alginic acid, microcrystalline cellulose, croscarmellose sodium, crospovidone, polacrilin potassium, sodium starch glycolate, starch, pregelatinized starch.

Tablet and/or capsule lubricants, like calcium stearate, glyceryl behenate, magnesium stearate, light mineral oil, polyethylene glycol, sodium stearyl fumarate, stearic acid, purified stearic acid, talc, hydrogenated vegetable oil, zinc stearate;

Tonicity agent, like dextrose, glycerin, mannitol, potassium chloride, sodium chloride Vehicle: flavored and/or sweetened aromatic elixir, compound benzaldehyde elixir, isoalcoholic elixir, peppermint water, sorbitol solution, syrup, tolu balsam syrup.

Vehicles, like oleaginous almond oil, corn oil, cottonseed oil, ethyl oleate, isopropyl myristate, isopropyl palmitate, mineral oil, light mineral oil, myristyl alcohol, α-tyldodecanol, olive oil, peanut oil, persic oil, sesame oil, soybean oil, squalane; solid carrier sugar spheres; sterile bacteriostatic water for injection, bacteriostatic sodium chloride injection, liquid triglycerides, liquid waxes, higher alcohols Water repelling agents, like cyclomethicone, dimethicone, simethicone;

Wetting and/or solubilizing agents, like benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaureate, sorbitan monooleate, sorbitan monopalmitate, sorbitan monostearate, tyloxapol;

The crystals may be combined with a polymeric carrier to provide for stability and/or sustained release. Such polymers include biocompatible and biodegradable polymers.

A polymeric carrier may be a single polymer type or it may be composed of a mixture of polymer types. Nonlimiting examples of polymeric carriers have already been stated above.

Examples of preferred ingredients or excipients include:

salts of amino acids such as glycine, arginine, aspartic acid, glutamic acid, lysine, asparagine, glutamine, proline, histidine;

monosaccharides, such as glucose, fructose, galactose, mannose, arabinose, xylose, ribose;

disaccharides, such as lactose, trehalose, maltose, sucrose;

polysaccharides, such as maltodextrins, dextrans, starch, glycogen;

alditols, such as mannitol, xylitol, lactitol, sorbitol;

glucuronic acid, galacturonic acid;

cyclodextrins, such as methyl cyclodextrin, hydroxypropyl-(3-cyclodextrin)

inorganic salts, such as sodium chloride, potassium chloride, magnesium chloride, phosphates of sodium and potassium, boric acid ammonium carbonate and ammonium phosphate;

organic salts, such as acetates, citrate, ascorbate, lactate;

emulsifying or solubilizing agents like acacia, diethanolamine, glyceryl monostearate, lecithin, monoethanolamine, oleic acid, oleyl alcohol, poloxamer, polysorbates, sodium lauryl sulfate, stearic acid, sorbitan monolaurate, sorbitan monostearate, and other sorbitan derivatives, polyoxyl derivatives, wax, polyoxyethylene derivatives, sorbitan derivatives; and viscosity increasing reagents like agar, alginic acid and its salts, guar gum, pectin, polyvinyl alcohol, polyethylene oxide, cellulose and its derivatives propylene carbonate, polyethylene glycol, hexylene glycol and tyloxapol.

Formulations described herein also comprise an effective amount of crystalline antibody. In particular, the formulations of the invention may include a "therapeutically effective amount" or a "prophylactically effective amount" of antibody crystals of the invention. A "therapeutically effective amount" refers to an amount effective, at dosages and for periods of time necessary, to achieve the desired therapeutic result. A "therapeutically effective amount" of the antibody crystals may vary according to factors such as the disease state, age, sex, and weight of the individual, and the ability of the antibody to elicit a desired response in the individual. A therapeutically effective amount is also one in which any toxic or detrimental effects of the antibody are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Suitable dosages can readily be determined using standard methodology. The antibody is suitably administered to the patient at one time or over a series of treatments. Depending on the above mentioned factors, about 1 µg/kg to about 50 mg/kg, as for example 0.1-20 mg/kg of antibody is an initial candidate dosage for administration to the patient, whether, for example, by one or more separate administrations, or by continuous infusion. A typical daily or weekly dosage might range from about 1 µg/kg to about 20 mg/kg or more, depending on the condition, the treatment is repeated until a desired suppression of disease symptoms occurs. However, other dosage regimens may be useful. In some cases, formulations comprise a concentration of antibody of at least about 1 g/L or greater when resolubilized. In other embodiments, the antibody concentration is at least about 1 g/L to about 100 g/L when resolubilized.

Crystals of an antibody, or formulations comprising such crystals, may be administered alone or as part of a pharmaceutical preparation. They may be administered by parenteral, oral or topical routes. For example, they may be administered by oral, pulmonary, nasal, aural, anal, dermal, ocular, intravenous, intramuscular, intraarterial, intraperitoneat, mucosal, sublingual, subcutaneous, transdermal, topical or intracranial routes, or into the buccal cavity. Specific examples of administration techniques comprise pulmonary inhalation, intralesional application, needle injection, dry powder inhalation, skin electroporation, aerosol delivery, and needle-free injection technologies, including needle-free subcutaneous administration.

The present invention will now be explained in more detail by means of the following, non-limiting, illustrative examples. Guided by the general part of the description and on the basis of his general knowledge a skilled reader will be enabled to provide further embodiments to the invention without undue experimentation.

EXPERIMENTAL PART

A. Materials a) Protein

Frozen monoclonal antibody (mAb) D2E7 was obtained from Abbott Laboratories. All experiments were performed from a drug product lot where the original mAb concentration was 50 mg/ml.

b) Fine Chemicals

Sodium acetate was obtained from Grüssing GmbH, Filsum. Polyethyleneglycols of different polymerization grades were obtained from Clariant GmbH, Sulzbach. Furthermore, commercial crystallization screens and reagents (Hampton Research, Nextal Biotechnologies) were used for certain microscale experiments. All other chemicals were from Sigma-Aldrich, Steinheim, or Merck, Darmstadt.

B. General Methods a) Thawing of D2E7 Drug Substance

D2E7 was thawed at 25° C. in agitated water baths.

b) Buffer Exchange—Method A

An aliquot of D2E7 solution was pipetted into a 30 KDa MWCO Vivaspin 20 concentrator (Vivascience). The protein sample was diluted with the new buffer in a ratio of 1:10, and by centrifugation at 5,000×g at 4° C. (Sigma 4 K 15 lab centrifuge) the sample volume was brought back to the original sample volume. The dilution/centrifugation steps were repeated once, resulting in a dilution of 1:100 of the original sample buffer. After adjustment of protein concentration, the solution was sterile filtered through a 0.2 µm syringe driven filter unit.

b) Buffer Exchange—Method B

An aliquot of D2E7 solution was placed into a SLIDE-A-LYZER dialysis cassette (Pierce Biotechnology Inc.). The dialysis cassette was placed into a beaker containing the buffer of choice, and the buffer exchange was performed at 4°

C. overnight with stirring. After adjustment of protein concentration, the solution was sterile filtered through a 0.2 μm syringe driven filter unit.

c) OD280—Protein Concentration Measurements

A ThermoSpectronics UV1 device was used to assess protein concentration at a wavelength of 280 nm, applying an extinction coefficient of 1.39 $cm^2$ $mg^{-1}$. For this purpose, aliquots of crystallization slurries were centrifuged at 14,000 rpm, and residual protein concentration was determined in the supernatant.

d) pH Measurements pH measurements were conducted by using a Mettler Toledo MP220 pH meter. Inlab 413 electrodes and Inlab 423 microelectrodes were utilized.

e) Crystallization Methods e1) Microscale Crystallization—Sitting Drop Vapor Diffusion Hydra II Initial crystallization screens were performed using a Hydra II crystallization robot and Greiner 96 well plates (three drop wells, Hampton Research). After setting up the plates, the wells were sealed with Clearseal film (Hampton Research).

e2) Microscale Crystallization—Hanging Drop Vapor Diffusion

Hanging drop vapor diffusion experiments were conducted using VDX plates (with sealant, Hampton Research) and OptiClear plastic cover slides (squares, Hampton Research) or siliconized glass cover slides (circle, Hampton Research), respectively. After preparation of reservoir solutions, one drop of reservoir solution was admixed with one drop of the protein solution on a cover slide, and the well was sealed with the inverted cover slide in such a way that the drop was hanging above the reservoir.

e3) Batch Crystallization—Method A (24 Well Plate)

Batch crystallization was performed by admixing the protein solution with an equal amount of crystallization buffer (500 μl) in a well. The well was subsequently sealed with adhesive tape to prevent water evaporation.

e4) Batch Crystallization—Method B (Eppendorff Reaction Tube)

Batch crystallization was performed by admixing the protein solution with an equal amount of crystallization buffer in a 1.5 mL or a 2 mL Eppendorff reaction tube.

e5) Batch Crystallization—Method C (Falcon Tubes, Agitation)

Batch crystallization was performed by admixing the protein solution with an equal amount of crystallization buffer in a 50 mL Falcon tube. Right after closing, the tube was put on a laboratory shaker (GFL 3013 or GFL 3015) or was alternatively agitated by tumbling. By application of these methods, introduction of stirrers into the sample was avoided.

e6) Batch Crystallization—Method D (1 Liter Polypropylene Container)

Batch crystallization was performed by admixing the protein solution with an equal amount of crystallization buffer in a sterilized 1 liter polypropylene bottle. Right after closing, the container was stored at ambient temperature without agitation. By application of this method, introduction of stirrers into the sample was avoided.

f) SDS-PAGE

Samples were prepared by adjusting protein concentration to 8 μg/20 μL. The samples were diluted with an SDS/Tris/Glycerine buffer containing bromphenolblue.

Qualitative SDS PAGE analysis was performed using Invitrogen NuPage 10% Bis-Tris Gels, NuPage MES SDS Running Buffer and Mark12 Wide Range Protein Standards. 20 μL of sample was pipetted into a gel pocket. After running the gel and fixation with acetic acid/methanol reagent, staining was performed using the Novex Colloidal Blue Stain Kit. Gels were dried using Invitrogen Gel-Dry drying solution.

g) Light Microscopy

Crystals were observed using a Zeiss Axiovert 25 or a Nikon Labophot microscope. The latter was equipped with a polarization filter set and a JVC TK C1380 color video camera.

h) SE-HPLC

Aggregation levels of D2E7 samples were assessed by SE-HPLC. A Dionex P680 pump, ASI-100 autosampler and UVD170U detector device were used. Aggregated species were separated from the monomer by an Amersham Bioscience Superose 6 10/300 GL gel filtration column, applying a validated Abbott standard protocol (CL16-PS-02, Adalimumab purity).

C. Vapor Diffusion Crystallization Experiments

Concentration values given in the following examples are initial values referring to the antibody solution and the reservoir solution before mixing of the two solutions.

All pH values, if not described otherwise, refer to the pH of an acetate buffer stock before it was combined with other substances, like the crystallization agent.

All buffer molarities, if not described otherwise, refer to sodium acetate concentrations in a stock solution before pH adjustment, typically performed using acetic acid glacial.

Example 1

PEG 4,000/Sodium Acetate Grid Screen in Hanging Drop Vapor Diffusion Mode

D2E7 was buffered into a buffer containing around 0.1 M sodium acetate at a pH of around 5.2. The protein concentration was adjusted to 10 mg/mL.

A greased VDX plate and square OptiClear plastic cover slides were used. 500 μL of a particular reservoir solution was prepared by admixing acetate buffer, 50% w/v PEG 4,000 solution and Milli Q water (fully desalted and optionally pre-destilled) in each well. In this example, the acetate buffer molarity was kept constant at around 0.1 M, and PEG 4,000 was varied from around 6% w/v to around 28% w/v in 2% steps. The pH was around 5.2 throughout. Each condition was assessed in duplicate. Around 1 μL of protein solution was admixed with around 1 μL of a particular reservoir solution on a square OptiClear plastic cover slide, and the well was sealed with the inverted slide, generating a hanging drop experiment. The plates were stored at ambient temperature. Microscopy of the drops was performed multiple times during the following thirty days. The conditions were classified into clear drops, drops containing random precipitation, drops containing crystals and drops containing mixtures of precipitated species and crystals.

Results:

From the 24 wells assessed, no crystals were observed.

Example 2

PEG 4,000/Sodium Acetate Grid Screen in Hanging Drop Vapor Diffusion Mode, Different Protein Concentration D2E7 was buffered into a buffer containing around 0.1 M sodium acetate at a pH of around 5.2. The protein concentration was adjusted to 50 mg/mL. Except for the protein concentration the process conditions were identical with those of Example 1.
Results:
From the 24 wells assessed, no crystals were observed.

Example 3

PEG 400/Sodium Acetate Grid Screen in Hanging Drop Vapor Diffusion Mode

D2E7 was buffered into a buffer containing around 0.1 M sodium acetate at a pH of around 5.2. The protein concentration was adjusted to 10 mg/mL.

A greased VDX plate and square OptiClear plastic cover slides were used. 500 µL of a particular reservoir solution was prepared by admixing acetate buffer, 50% w/v PEG 400 solution and Milli Q water in each well. In this example, the acetate buffer molarity was kept constant at around 0.1 M, and PEG 400 was varied from around 30% w/v to around 40% w/v in 2% steps. The pH was around 5.2 throughout. Each condition was assessed in duplicate. Around 1 µL of protein solution was admixed with around 1 µL of a particular reservoir solution on a square OptiClear plastic cover slide, and the well was sealed with the inverted slide, generating a hanging drop experiment. The plates were stored at ambient temperature. Microscopy of the drops was performed multiple times during the following thirty days. The conditions were classified into clear drops, drops containing random precipitation, drops containing crystals and drops containing mixtures of precipitated species and crystals.
Results:
From the 12 wells assessed, no crystals were observed.

Example 4

PEG 400/Sodium Acetate Grid Screen in Hanging Drop Vapor Diffusion Mode, Different Protein Concentration D2E7 was buffered into a buffer containing around 0.1 M sodium acetate at a pH of around 5.2. The protein concentration was adjusted to 50 mg/mL. Except for the protein concentration the process conditions were identical with those of Example 3.
Results:
From the 12 wells assessed, no crystals were observed.

Example 5

PEG 10,000/Sodium Acetate Grid Screen in Hanging Drop Vapor Diffusion Mode

D2E7 was buffered into a buffer containing around 0.1 M sodium acetate at a pH of around 5.2. The protein concentration was adjusted to 10 mg/mL.

A greased VDX plate and square OptiClear plastic cover slides were used. 500 µL of a particular reservoir solution was prepared by admixing acetate buffer, 50% w/v PEG 400 solution and Milli Q water in each well. In this example, the acetate buffer molarity was kept constant at around 0.1 M, and PEG 10,000 was varied from around 4% w/v to around 14% w/v in 2% steps. The pH was around 5.2 throughout. Each condition was assessed in duplicate. Around 1 µL of protein solution was admixed with around 1 µL of a particular reservoir solution on a square OptiClear plastic cover slide, and the well was sealed with the inverted slide, generating a hanging drop experiment. The plates were stored at ambient temperature. Microscopy of the drops was performed multiple times during the following thirty days. The conditions were classified into clear drops, drops containing random precipitation, drops containing crystals and drops containing mixtures of precipitated species and crystals.
Results:
From the 12 wells assessed, no crystals were observed.

Example 6

PEG 10,000/Sodium Acetate Grid Screen in Hanging Drop Vapor Diffusion Mode, Different Protein Concentration D2E7 was buffered into a buffer containing around 0.1 M sodium acetate at a pH of around 5.2. The protein concentration was adjusted to 45 to 55 mg/mL, preferably 50 mg/mL. Except for the protein concentration the process conditions were identical with those of Example 5.
Results:
From the 12 wells assessed, no crystals were observed.

Example 7

PEG 400/Sodium Acetate Grid Screen in Hanging Drop Vapor Diffusion Mode, Different Set Up D2E7 was buffered into a buffer containing around 0.1 M sodium acetate at a pH of around 5.2. The protein concentration was adjusted to 10 mg/mL.

A greased VDX plate and square OptiClear plastic cover slides were used. 500 µL of a particular reservoir solution was prepared by admixing acetate buffer, 50% w/v PEG 10,000 solution and Milli Q water in each well. In this example, the acetate buffer molarity was kept constant at around 0.1 M, and PEG 400 was around 32% w/v and around 34% w/v. The pH was around 4.2, 4.7, 5.2, 5.7, 6.2 or 6.7. Each condition was assessed in duplicate. Around 1 µL of protein solution was admixed with around 1 µL of a particular reservoir solution on a square OptiClear plastic cover slide, and the well was sealed with the inverted slide, generating a hanging drop experiment. The plates were stored at ambient temperature. Microscopy of the drops was performed multiple times during the following thirty days. The conditions were classified into clear drops, drops containing random precipitation, drops containing crystals and drops containing mixtures of precipitated species and crystals.
Results:
From the 24 wells assessed, no crystals were observed.

Example 8

PEG 400/Sodium Acetate Grid Screen in Hanging Drop Vapor Diffusion Mode, Different Protein Concentration and Set Up D2E7 was buffered into a buffer containing around 0.1 M sodium acetate at a pH of around 5.2. The protein concentration was adjusted to 50 mg/mL. Except for the protein concentration the process conditions were identical with those of Example 7.

Results:
From the 24 wells assessed, no crystals were observed.

Example 9

PEG 400/Sodium Acetate Grid Screen in Hanging Drop Vapor Diffusion Mode, Different Set Up D2E7 was buffered into a buffer containing around 0.1 M sodium acetate at a pH of around 5.2. The protein concentration was adjusted to 10 mg/mL.

A greased VDX plate and square OptiClear plastic cover slides were used. 500 µL of a particular reservoir solution was prepared by admixing acetate buffer, 50% w/v PEG 400 solution and Milli Q water in each well. In this example, the acetate buffer molarity was used at around 0.025 M, 0.05 M, 0.075 M, 0.15 M, 0.2 M or 0.25 M. PEG 400 was varied from around 32% w/v to around 34% w/v. The pH was around 5.7 or 4.2. Each condition was assessed in duplicate. Around 1 µL of protein solution was admixed with around 1 µL of a particular reservoir solution on a square OptiClear plastic cover slide, and the well was sealed with the inverted slide, generating a hanging drop experiment. The plates were stored at ambient temperature. Microscopy of the drops was performed multiple times during the following thirty days. The conditions were classified into clear drops, drops containing random precipitation, drops containing crystals and drops containing mixtures of precipitated species and crystals.
Results:
From the 48 wells assessed, no crystals were observed.

Example 10

PEG 400/Sodium Acetate Grid Screen in Hanging Drop Vapor Diffusion Mode, Different Set Up D2E7 was buffered into a buffer containing around 0.1 M sodium acetate at a pH of around 5.2. The protein concentration was adjusted to 10 mg/mL.

A greased VDX plate and square OptiClear plastic cover slides were used. 500 µL of a particular reservoir solution was prepared by admixing acetate buffer, 50% w/v PEG 400 solution and Milli Q water in each well. In this example, the acetate buffer molarity was used at around 0.025 M, 0.05 M or 0.1 M. PEG 400 was around 28% w/v or around 30% w/v. The pH was around 5.2, 5.7, 6.2 or 6.7. Each condition was assessed in duplicate. Around 1 µL of protein solution was admixed with around 1 µL of a particular reservoir solution on a square OptiClear plastic cover slide, and the well was sealed with the inverted slide, generating a hanging drop experiment. The plates were stored at ambient temperature. Microscopy of the drops was performed multiple times during the following thirty days. The conditions were classified into clear drops, drops containing random precipitation, drops containing crystals and drops containing mixtures of precipitated species and crystals.
Results:
From the 48 wells assessed, no crystals were observed.

Example 11

PEG 400 Combined with PEG 4,000/Sodium Acetate Grid Screen in Hanging Drop Vapor Diffusion Mode D2E7 was buffered into a buffer containing around 0.1 M sodium acetate at a pH of around 5.2. The protein concentration was adjusted to 10 mg/mL.

A greased VDX plate and square OptiClear plastic cover slides were used. 500 µL of a particular reservoir solution was prepared by admixing acetate buffer, 50% w/v PEG 4,000 solution and Milli Q water in each well. In this example, the acetate buffer molarity was kept constant at around 0.1 M, and PEG 4,000 was varied from around 4% w/v to around 8% w/v in 2% steps. Simultaneously, PEG 400 was added to the PEG 4,000/acetate solutions at concentrations of around 24% w/v, 26% w/v, 28% w/v or 30% w/v. The pH was around 5.2 throughout. Each condition was assessed in duplicate. Around 1 µL of protein solution was admixed with around 1 µL of a particular reservoir solution on a square OptiClear plastic cover slide, and the well was sealed with the inverted slide, generating a hanging drop experiment. The plates were stored at ambient temperature. Microscopy of the drops was performed multiple times during the following thirty days. The conditions were classified into clear drops, drops containing random precipitation, drops containing crystals and drops containing mixtures of precipitated species and crystals.
Results:
From the 24 wells assessed, no crystals were observed.

Example 12

PEG 400 Combined with PEG 4,000/Sodium Acetate Grid Screen in Hanging Drop Vapor Diffusion Mode, Different Set Up D2E7 was buffered into a buffer containing around 0.1 M sodium acetate at a pH of around 5.2. The protein concentration was adjusted to 10 mg/mL.

A greased VDX plate and square OptiClear plastic cover slides were used. 500 µL of a particular reservoir solution was prepared by admixing acetate buffer, 50% w/v PEG 4,000 solution and Milli Q water in each well. In this example, the acetate buffer molarity was kept constant at around 0.1 M, and PEG 4,000 was varied from around 4% w/v to around 8% w/v in 2% steps. Simultaneously, PEG 400 was added to the PEG 4,000/acetate solutions at concentrations of around 30% w/v, 32% w/v, 34% w/v or 36% w/v. The pH was around 4.2 throughout. Each condition was assessed in duplicate. Around 1 µL of protein solution was admixed with around 1 µL of a particular reservoir solution on a square OptiClear plastic cover slide, and the well was sealed with the inverted slide, generating a hanging drop experiment. The plates were stored at ambient temperature. Microscopy of the drops was performed multiple times during the following thirty days. The conditions were classified into clear drops, drops containing random precipitation, drops containing crystals and drops containing mixtures of precipitated species and crystals.
Results:
From the 24 wells assessed, no crystals were observed.

Example 13

PEG 4,000/Sodium Acetate Grid Screen in Hanging Drop Vapor Diffusion Mode, Different Set Up D2E7 was buffered into a buffer containing around 0.1 M sodium acetate at a pH of around 6.5, 6.0, 5.5, 5.0, 4.5 or 4.0. The protein concentration was adjusted to 10 mg/mL.

A greased VDX plate and square OptiClear plastic cover slides were used. 500 µL of a particular reservoir solution was prepared by admixing acetate buffer, 50% w/v PEG 4,000 solution and Milli Q water in each well. In this example, the acetate buffer molarity was kept constant at around 0.1 M, and PEG 4,000 was varied from around 4% w/v to around 26% w/v in 2% steps. The pH of the acetate buffer used was the same as the corresponding protein buffer. Each condition was assessed in duplicate. Around 1 μL of protein solution was admixed with around 1 μL of a particular reservoir solution on a square OptiClear plastic cover slide, and the well was sealed with the inverted slide, generating a hanging drop experiment. The plates were stored at ambient temperature. Microscopy of the drops was performed multiple times during the following thirty days. The conditions were classified into clear drops, drops containing random precipitation, drops containing crystals and drops containing mixtures of precipitated species and crystals.
Results:
From the 144 wells assessed, no crystals were observed.

Example 14

PEG 4,000/Sodium Acetate Grid Screen in Hanging Drop Vapor Diffusion Mode, Different Set Up The experimental conditions were identical to Example 13, except for the acetate buffer molarity, which was kept constant at around 0.2 M (molarity of precipitation buffer)
Results:
From the 144 wells assessed, no crystals were observed.

Example 15

PEG 4,000/Sodium Acetate Grid Screen in Hanging Drop Vapor Diffusion Mode, Different Set Up The experimental conditions were identical to Example 13, except for the acetate buffer molarity which was kept constant at 0.1 M (molarity of precipitation buffer).
Results:
From the 144 wells assessed, no crystals were observed.

Example 16

PEG 4,000/Sodium Acetate Grid Screen in Hanging Drop Vapor Diffusion Mode, Different Set Up The experimental conditions were identical to Example 13, except for the acetate buffer molarity which was kept constant at around 0.4 M (molarity of precipitation buffer).
Results:
From the 144 wells assessed, no crystals were observed.

Example 17

PEG 4,000/Sodium Acetate Bulk Experiments

D2E7 was buffered into a buffer containing around 0.1 M sodium acetate at a pH of around 5.5. The protein concentration was adjusted to 10 mg/mL.
Four aliquots of 500 μL each were pipetted into four Eppendorff reaction tubes. A 24% PEG 4,000 in 0.1 M sodium acetate buffer at pH 5.5 solution was titrated to the protein solutions until the solution became slightly opaque. Subsequently, water was pipetted to the solutions just until the solutions became clear again. This method is referred to as bulk crystallization. Titration was performed at ambient temperature for two samples and at 4° C. for the two other samples. Subsequently, one of each pair of samples was stored at ambient temperature or at 4° C., respectively. Microscopy of 1 μL aliquots of the samples was performed multiple times during the following week
Results:
From the four samples, none rendered crystals.

Example 18

PEG 4,000/Sodium Acetate Grid Screen in Hanging Drop Vapor Diffusion Mode, Different Temperature The experimental conditions were identical to Example 13. However, the tubes were set up and stored at 4° C.
Results:
From the 144 wells assessed, no crystals were observed.

Example 19

PEG 4,000/Sodium Acetate Grid Screen in Hanging Drop Vapor Diffusion Mode, Different Protein Concentration Except for the protein concentration, which was adjusted to 5 mg/mL the experimental conditions were identical to Example 13.
Results:
From the 144 wells assessed, no crystals were observed.

Example 20

Ammonium Sulfate/Sodium Acetate Grid Screen in Hanging Drop Vapor Diffusion Mode D2E7 was buffered into a buffer containing around 0.1 M sodium acetate at a pH of around 5.5. The protein concentration was adjusted to 10 mg/mL.
A greased VDX plate and square OptiClear plastic cover slides were used. 500 μL of a particular reservoir solution was prepared by admixing acetate buffer, ammonium sulfate stock solution and Milli Q water in each well. In this example, the acetate buffer molarity was kept constant at around 0.1 M, and the ammonium sulfate concentration was varied from 0.5 M to 2.5 M in steps of 0.25 M. The pH of the acetate buffer was around 5.5 throughout. Each condition was assessed in duplicate. Around 1 μL of protein solution was admixed with around 1 μL of a particular reservoir solution on a square OptiClear plastic cover slide, and the well was sealed with the inverted slide, generating a hanging drop experiment. The plates were set up and stored at ambient temperature. Microscopy of the drops was performed multiple times during the following two weeks. The conditions were classified into clear drops, drops containing random precipitation, drops containing crystals and drops containing mixtures of precipitated species and crystals.
Results:
From the 18 wells assessed, no crystals were observed.

Example 21

Sodium Chloride/Sodium Acetate Grid Screen in Hanging Drop Vapor Diffusion Mode

D2E7 was buffered into a buffer containing around 0.1 M sodium acetate at a pH of around 5.5. The protein concentration was adjusted to 10 mg/mL.
A greased VDX plate and square OptiClear plastic cover slides were used. 500 μL of a particular reservoir solution was prepared by admixing acetate buffer, sodium chloride stock solution and Milli Q water in each well. In this example, the acetate buffer molarity was kept constant at around 0.1 M, and the sodium chloride concentration was varied from 1.5 M to 2.5 M, varied in steps of 0.5 M. The pH of the acetate buffer was around 5.5 throughout. Each condition was assessed in duplicate. Around 1 µL of protein solution was admixed with around 1 µL of a particular reservoir solution on a square OptiClear plastic cover slide, and the well was sealed with the inverted slide, generating a hanging drop experiment. The plates were set up and stored at ambient temperature. Microscopy of the drops was performed multiple times during the following two weeks. The conditions were classified into clear drops, drops containing random precipitation, drops containing crystals and drops containing mixtures of precipitated species and crystals.

Results:
From the 6 wells assessed, no crystals were observed.

Example 22

PEG 4,000/Sodium Acetate Grid Screen in Hanging Drop Vapor Diffusion Mode, Influence of Detergents D2E7 was buffered into a buffer containing around 0.1 M sodium acetate at a pH of around 5.5. The protein concentration was adjusted to 5 mg/mL.

A greased VDX plate and square OptiClear plastic cover slides were used. 500 µL of a particular reservoir solution was prepared by admixing acetate buffer, 50% w/v PEG 4,000 solution and Milli Q water in each well. In this example, the acetate buffer molarity was kept constant at around 0.1 M, and PEG 4,000 was varied from around 10% w/v to around 20% w/v in 2% steps. The pH of the acetate buffer was around 5.5 throughout. Furthermore, polysorbate 20, polysorbate 80 and Pluronic F 68 were added to any resulting buffer as described above at concentrations of 0%, 0.02% and 0.1%, respectively. Around 1 µL of protein solution was admixed with around 1 µL of a particular reservoir solution on a square OptiClear plastic cover slide, and the well was sealed with the inverted slide, generating a hanging drop experiment. The plates were set up and stored at ambient temperature. Microscopy of the drops was performed multiple times during the following two weeks. The conditions were classified into clear drops, drops containing random precipitation, drops containing crystals and drops containing mixtures of precipitated species and crystals.

Results:
From the 84 wells assessed, no crystals were observed. No influence of the assessed detergents on the behaviour of the crystallization system could be observed.

Example 23

Zinc Acetate/Sodium Acetate Grid Screen in Hanging Drop Vapor Diffusion Mode

D2E7 was buffered into a buffer containing around 0.1 M sodium acetate at a pH of around 5.5. The protein concentration was adjusted to 10 mg/mL.

A greased VDX plate and square OptiClear plastic cover slides were used. 500 µL of a particular reservoir solution was prepared by admixing acetate buffer, zinc acetate stock solution and Milli Q water in each well. In this example, the acetate buffer molarity was kept constant at around 0.1 M, and the zinc acetate concentration was varied from 0.1 M to 0.9 M in steps of around 0.2 M. The pH of the acetate buffer was around 5.5 throughout. Each condition was assessed in duplicate. Around 1 µL of protein solution was admixed with around 1 µL of a particular reservoir solution on a square OptiClear plastic cover slide, and the well was sealed with the inverted slide, generating a hanging drop experiment. The plates were set up and stored at ambient temperature. Microscopy of the drops was performed multiple times during the following two weeks. The conditions were classified into clear drops, drops containing random precipitation, drops containing crystals and drops containing mixtures of precipitated species and crystals.

Results:
From the 12 wells assessed, no crystals were observed.

Example 24

Broad Screening of Conditions in Vapor Diffusion Mode

D2E7 was buffered into a 20 mM HEPES/150 mM sodium chloride buffer at pH 7.4. The protein concentration was adjusted to 5 mg/mL, 10 mg/mL, or 20 mg/mL.

Using the Hydra II crystallization robot, 96 well Greiner plates were set up at ambient temperature, using several commercially available crystallization screens. The protein solution and the crystallization agent were admixed in a ratio of around 1:1, preferably 1:1.

The following screens were used:
Hampton Crystal Screen 1 & 2 (Hampton Research),
Hampton Index Screen (Hampton Research),
Hampton SaltRX Screen (Hampton Research),
Nextal The Classics, The Classics Lite, The PEGs, The Anions, The pH clear and The Ammonium sulfate (all from Nextal Biotechnologies).

After addition of protein to the crystallization agent (three drops per condition, containing the three different protein concentrations as described above), the plates were sealed with Clearseal film. Each plate was set up in quadruplicate and then stored at ambient temperature, 4° C., 27° C. and 37° C., respectively. Microscopy of the drops was performed after five days and twelve days, respectively. The conditions were classified into clear drops, drops containing random precipitation, drops containing crystals and drops containing mixtures of precipitated species and crystals.

Results:
From the 864 commercial conditions evaluated, 2 rendered crystals at protein concentrations and temperatures as defined below, at least after two weeks.

0.1 M sodium acetate anhydrous pH 4.6, 0.9 M sodium dihydrogen phosphate, 0.9 M potassium dihydrogen phosphate (=Nextal The Anions, E3), 10 or 20 mg/mL, and 27° C., or 20 mg/mL and 37° C.

0.1 M Bis-Tris Propane pH 7.0, 1.5 M ammonium sulfate (=Hampton SaltRX, F2), 5, 10, or 20 mg/mL. and 27° C.

The crystals showed needle cluster-like morphologies.

The following conditions from commercially available screens did not render crystals. For detailed solution compositions, please refer to www.hamptonresearch.com and www.nextalbiotech.com:
Hampton Crystal Screen 1—all conditions (48)
Hampton Crytsal Screen 2—all conditions (48)
Hampton Index Screen—all conditions (96)
Hampton SaltRX Screen—all conditions despite "F2" (95)
Nextal—The Classics—all conditions (96)
Nextal—The Classics Lite—all conditions (96)
Nextal—The PEGs—all conditions (96)
Nextal—The Anions—all conditions despite "E3" (95)

Nextal—The pH Clear—all conditions (96)
Nextal—The AmmoniumSulfate—all conditions (96)

Example 25

PEG 4,000/Sodium Acetate Grid Screen in Hanging Drop Vapor Diffusion Mode, Different Set Up D2E7 was buffered into a 20 mM HEPES/150 mM sodium chloride buffer at pH 7.4. The protein concentration was adjusted to 5 mg/mL, 10 mg/mL, or 20 mg/mL.

A greased VDX plate and circle siliconized glass cover slides were used. 500 µL of a particular reservoir solution was prepared by admixing acetate buffer, 50% w/v PEG 4,000 solution and Milli Q water in each well. In this example, the acetate buffer molarity was kept constant at around 0.1 M, and PEG 4,000 concentration was varied from 4% to 26% in 2% steps. The pH was around 5.5 throughout. Each condition was set up with the three protein concentrations as described above. Around 1 µL of protein solution was admixed with around 1 µL of a particular reservoir solution on a circle siliconized glass cover slide, and the well was sealed with the inverted slide, generating a hanging drop experiment. The plates were stored at ambient temperature. Microscopy of the drops was performed after six days. The conditions were classified into clear drops, drops containing random precipitation, drops containing crystals and drops containing mixtures of precipitated species and crystals.
Results:
From the 72 wells assessed, no crystals were observed.

Example 26

Hanging Drop Vapor Diffusion Experiments Applying the Hampton Detergent Screen

D2E7 was buffered into a 20 mM HEPES/150 mM sodium chloride buffer at pH 7.4. The protein concentration was adjusted to 5 mg/mL.

A greased VDX plate and circle siliconized glass cover slides were used. 500 µL of a particular reservoir solution was prepared by admixing acetate buffer, 50% w/v PEG 4,000 solution and Milli Q water in each well. In this example, the acetate buffer molarity was kept constant at around 0.1 M, and the PEG 4,000 concentration around 12% w/v or 14% w/v. The pH was around 5.5 throughout. Around 4 µL of protein solution was admixed with around 1 µL of a particular detergent solution of the Hampton screen on a circle siliconized glass cover slide. The drop was subsequently admixed with 5 µL of a particular reservoir solution, and the well was sealed with the inverted slide, generating a hanging drop experiment. The plates were stored at ambient temperature. Microscopy of the drops was performed after six days. The conditions were classified into clear drops, drops containing random precipitation, drops containing crystals and drops containing mixtures of precipitated species and crystals.
Results:
From the 144 wells assessed, no crystals were observed.

Example 27

Hanging Drop Vapor Diffusion Using Hampton PEG/Ion Screen

D2E7 was buffered into a 20 mM HEPES/150 mM sodium chloride buffer at pH 7.4. The protein concentration was adjusted to 5 mg/mL or 10 mg/mL.

Greased VDX plates and circle siliconized glass cover slides were used. 500 µL of each of the 48 buffer formulations was pipetted into a well and admixed with 250 µL of Milli Q water, respectively. Around 1 µL of protein sample was pipetted onto a cover slide and subsequently admixed with around 1 µL of the reservoir solution of a particular well. The well was sealed with the inverted cover slide, generating a hanging drop experiment. The plates were stored at ambient temperature. Microscopy of the drops was performed multiple times during the following seven days. The conditions were classified into clear drops, drops containing random precipitation, drops containing crystals and drops containing mixtures of precipitated species and crystals.
Results:
From the 96 conditions tested, no crystals were observed.

Example 28

Hanging Drop Vapor Diffusion Using Hampton PEG/Ion Screen, Different Set Up

D2E7 was buffered into a 20 mM HEPES/150 mM sodium chloride buffer at pH 7.4. The protein concentration was adjusted to 5 mg/mL.

The experimental conditions were identical with those of Example 27 with the exception that 500 µL of each of the 48 buffer formulations was pipetted into a well and admixed with 500 µL of Milli Q water, respectively.
Results:
From the 48 conditions tested, no crystals were observed.

Example 29

Hanging Drop Vapor Diffusion Using Hampton Low Ionic Strength Screen

D2E7 was buffered into a 20 mM HEPES/150 mM sodium chloride buffer at pH 7.4. The protein concentration was adjusted to 5 mg/mL.

Greased VDX plates and circle siliconized glass cover slides were used. 1 mL of 24% w/v PEG 3,350 dehydrant solution was pipetted into 108 wells, respectively. Around 2 µL of protein sample were pipetted onto a cover slide and subsequently admixed with around 1 µL of one of the 18 particular buffer reagents. Thereafter, around 2.5 µL of PEG 3,350 precipitant of one of six different concentrations was added to the drop. The wells were sealed with the inverted cover slides, generating 108 different hanging drop experiments.

The plates were stored at ambient temperature. Microscopy of the drops was performed multiple times during the following seven days. The conditions were classified into clear drops, drops containing random precipitation, drops containing crystals and drops containing mixtures of precipitated species and crystals.
Results:
From the 108 conditions tested, none rendered crystals.

Example 30

Ammonium Sulfate/Bis-Tris Propane Grid Screen in Hanging Drop Vapor Diffusion Mode D2E7 was buffered into a 20 mM HEPES/150 mM sodium chloride buffer at pH 7.4. The protein concentration was adjusted to 5 mg/mL, 10 mg/mL, or 20 mg/mL.

A greased VDX plate and circle siliconized glass cover slides were used. 500 µL of a particular reservoir solution was prepared by admixing ammonium sulfate stock solution, Bis-Tris propane stock solution and Milli Q water in each well. In this example, ammonium sulfate molarity was around 0.5 M, 1 M, 1.5 M or 2 M. The Bis-Tris Propane molarity was 0.1 M throughout, and the Bis-Tris Propane buffer pH was around 5.5, 6.0, 6.5, 7.0, 7.5 or 8.0. The resulting 24 conditions were assessed with all of the three protein concentrations as described above, and with storage at ambient temperature or storage at around 27° C., respectively. Around 1 µL of protein solution was admixed with around 1 µL of a particular reservoir solution on a circle siliconized glass cover slide, and the well was sealed with the inverted slide, generating a hanging drop experiment. The plates were stored at ambient temperature. Microscopy of the drops was performed after three days. The conditions were classified into clear drops, drops containing random precipitation, drops containing crystals and drops containing mixtures of precipitated species and crystals.

Results:
From the 144 conditions tested, none rendered crystals after three days.

Example 31

Sodium Potassium Dihydrogen Phosphate/Sodium Acetate Grid Screen in Hanging Drop Vapor Diffusion Mode D2E7 was buffered into a 20 mM HEPES/150 mM sodium chloride buffer at pH 7.4. The protein concentration was adjusted to 5 mg/mL, 10 mg/mL, or 20 mg/mL.

A greased VDX plate and square OptiClear plastic cover slides were used. 500 µL of a particular reservoir solution was prepared by admixing acetate buffer, sodium dihydrogen phosphate stock solution, potassium dihydrogen phosphate stock solution and Milli Q water in each well. In this example, the acetate buffer molarity was kept constant at around 0.1 M, and the acetate buffer pH was around 4.1, 4.6, 5.1 or 5.6.

The following combinations of sodium dihydrogen phosphate and potassium dihydrogen phosphate were applied:
around 0.3 M sodium dihydrogen phosphate and around 0.3 M potassium dihydrogen phosphate;
around 0.6 M sodium dihydrogen phosphate and around 0.6 M potassium dihydrogen phosphate;
around 0.9 M sodium dihydrogen phosphate and around 0.9 M potassium dihydrogen phosphate;
around 1.8 M sodium dihydrogen phosphate,
around 2.1 M sodium dihydrogen phosphate,
around 2.4 M sodium dihydrogen phosphate.

Each condition was set up with the three protein concentrations as described above. Around 1 µL of protein solution was admixed with around 1 µL of a particular reservoir solution on a square OptiClear plastic cover slide, and the well was sealed with the inverted slide, generating a hanging drop experiment. The plates were stored at ambient temperature. Microscopy of the drops was performed multiple times during the following month. The conditions were classified into clear drops, drops containing random precipitation, drops containing crystals and drops containing mixtures of precipitated species and crystals.

Results:
From the 72 wells assessed, the following crystallization buffers generated crystals in the shape of needle clusters:
around 0.9 M sodium dihydrogen phosphate and around 0.9 M potassium dihydrogen phosphate, at pH around 4.1;
around 1.8 M sodium dihydrogen phosphate without the potassium salt, at pH around 4.6.
Crystals were obtained with these conditions at all three protein concentrations.

Example 32

Sodium Potassium Dihydrogen Phosphate/Sodium Acetate Grid Screen in Hanging Drop Vapor Diffusion Mode, Different Temperature The experimental conditions were identical with those of Example 31, except that the storage temperature was increased to 30° C.

Results:
From the 72 wells assessed, following crystallization buffers generated crystals in the shape of needle clusters:
Protein concentration of around 5 mg/mL:
around 0.9 M sodium dihydrogen phosphate and around 0.9 M potassium dihydrogen phosphate at pH around 4.1;
around 1.8 M sodium dihydrogen phosphate without the potassium salt, at pH around 4.1.
around 1.8 M sodium dihydrogen phosphate without the potassium salt, at pH around 4.6.
Around 1.8 M sodium dihydrogen phosphate without the potassium salt, at pH around 5.1.
Protein concentration of around 10 mg/mL:
around 0.9 M sodium dihydrogen phosphate and around 0.9 M potassium dihydrogen phosphate, at pH around 4.1.
around 1.8 M sodium dihydrogen phosphate without the potassium salt, at pH around 4.6.
around 1.8 M sodium dihydrogen phosphate without the potassium salt, at pH around 5.1.
Protein concentration of around 20 mg/mL:
around 0.9 M sodium dihydrogen phosphate and around 0.9 M potassium dihydrogen phosphate at pH around 4.1 and
around 1.8 M sodium dihydrogen phosphate without the potassium salt, at pH around 4.1.

Discussion of Results of Vapor Diffusion Crystallization Experiments:

Crystallization experiments were initially performed using a well-described micro scale methodology. Since a PEG 4,000/sodium acetate buffer condition was described as a promising crystallization condition by other inventors who were working with different antibodies of different antigen specificity or origin, it was decided to start with these agents. It was found after extensive experimentation that PEG 4,000 in an acetate buffer did not provide crystals, at least at investigated combinations of factors influencing crystallization (protein concentration, precipitating agent concentration, buffer ionic strength and pH, temperature), and thus it was decided to continue with broad crystallization screens, thereby introducing a wide variety of chemicals into the screening process. Finally, it was surprisingly found that sodium dihydrogen phosphate in acetate buffer is a powerful crystallization agent for D2E7, which does not introduce any toxic reagent unacceptable from a pharmaceutical point of view.

D. Batch Crystallization Experiments

Concentration values given in the following examples are initial values referring to the antibody solution and the crystallization solution before mixing of the two solutions.

All pH values, if not described otherwise, refer to the pH of an acetate buffer stock before it was combined with other substances, like the crystallization agent.

All buffer molarities, if not described otherwise, refer to sodium acetate concentrations in a stock solution before pH adjustment, typically performed using acetic acid glacial.

Example 33

Sodium Potassium Dihydrogen Phosphate/Sodium Acetate Batch Crystallization at 800 µL Batch Volume D2E7 was buffered into a 20 mM HEPES/150 mM sodium chloride buffer at pH 7.4. The protein concentration was adjusted to 5 mg/mL, 10 mg/mL, or 20 mg/mL.

Batch crystallization was performed by admixing around 400 µL of each protein solution with an equal amount of crystallization solution in a 1.5 mL Eppendorff reaction tube. 400 µL of a particular crystallization solution was prepared by admixing acetate buffer, sodium dihydrogen phosphate stock solution, potassium dihydrogen phosphate stock solution and Milli Q water. In this example, the acetate buffer molarity was 0.1 M, and the acetate buffer pH was around 4.1. The following combination of sodium dihydrogen phosphate and potassium dihydrogen phosphate was used: around 0.9 M sodium dihydrogen phosphate and around 0.9 M potassium dihydrogen phosphate. The reaction tubes were stored at ambient temperature. Microscopy of 1 µL aliquots was performed after 11 days.

Results:

No crystals were observed after 11 days.

Example 34

Sodium Dihydrogen Phosphate/Sodium Acetate Batch Crystallization at 600 µL Batch Volume D2E7 was buffered into a 20 mM HEPES/150 mM sodium chloride buffer at pH 7.4. The protein concentration was adjusted to 10 mg/mL.

Batch crystallization was performed by admixing around 300 µL of the protein solution with an equal amount of crystallization solution in a 1.5 mL Eppendorff reaction tube. 300 µL of a particular crystallization solution was prepared by admixing acetate buffer, sodium dihydrogen phosphate stock solution and Milli Q water. In this example, the acetate buffer molarity was 0.1 M, and the acetate buffer pH was around 4.1. Sodium dihydrogen phosphate molarity was around 1.5 M, 1.8 M, 2.1 M and 2.4 M, respectively. The reaction tubes were stored at ambient temperature. Microscopy of 1 µL aliquots was performed after 11 days.

Results:

No crystals were observed after 11 days.

Example 35

Sodium Potassium Dihydrogen Phosphate/Sodium Acetate Grid Screen Batch Crystallization at 1 mL Batch Volume D2E7 was used without exchanging the buffer. Thus, the initial composition was D2E7 50 mg/mL, mannitol 12 mg/mL, polysorbate 80 1 mg/mL, citric acid monohydrate 1.305 mg/mL, sodium citrate 0.305 mg/mL, disodium hydrogen phosphate dihydrate 1.53 mg/mL, sodium dihydrogen phosphate dehydrate 0.86 mg/mL, and sodium chloride 6.16 mg/mL, pH 5.2.

D2E7 was brought to a concentration of around 10 mg/mL by dilution with Milli Q water.

Batch crystallization was performed by admixing around 500 µL of the protein solution with an equal amount of crystallization solution in well of a 24 well plate. 500 µL of a particular crystallization solution was prepared by admixing acetate buffer, sodium dihydrogen phosphate stock solution, potassium dihydrogen phosphate stock solution and Milli Q water in a well. In this example, the acetate buffer molarity was 0.1 M, and the acetate buffer pH was around 4.1, 4.6, 5.1 or 5.6. The following combinations of sodium dihydrogen phosphate and potassium dihydrogen phosphate were used:

around 0.7 M sodium dihydrogen phosphate and around 0.7 M potassium dihydrogen phosphate,
around 0.9 M sodium dihydrogen phosphate and around 0.9 M potassium dihydrogen phosphate,
around 1.8 M sodium dihydrogen phosphate without the potassium salt,
around 2.1 M sodium dihydrogen phosphate without the potassium salt,
around 2.4 M sodium dihydrogen phosphate without the potassium salt.

The wells were subsequently sealed after preparation of the crystallization mixture to prevent water evaporation. Microscopy of the plate was performed after 4 days.

Results:

No crystals were observed after 4 days.

Example 36

Sodium Potassium Dihydrogen Phosphate/Sodium Acetate Grid Screen Batch Crystallization at 1 mL Batch Volume D2E7 was buffered into a 20 mM HEPES/150 mM sodium chloride buffer at pH 7.4. The protein concentration was adjusted to 10 mg/mL.

Batch crystallization was performed by admixing around 500 µL of the protein solution with an equal amount of crystallization solution in well of a 24 well plate. 500 µL of a particular crystallization solution was prepared by admixing acetate buffer, sodium dihydrogen phosphate stock solution, potassium dihydrogen phosphate stock solution and Milli Q water in a well. In this example, the acetate buffer molarity was 0.1 M, and the acetate buffer pH was around 4.1 or 4.6. The following combinations of sodium dihydrogen phosphate and potassium dihydrogen phosphate were applied:

around 1.8 M sodium dihydrogen phosphate and around 0.8 M potassium dihydrogen phosphate,
around 2.2 M sodium dihydrogen phosphate and around 0.6 M potassium dihydrogen phosphate,
from around 2.6 M sodium dihydrogen phosphate to around 4.4 M sodium dihydrogen phosphate in 0.2 M steps without the potassium salt, respectively.

The wells were subsequently sealed after preparation of the crystallization mixture to prevent water evaporation. Microscopy of the plate was performed multiple times during the following week. Furthermore, the crystal yield of three batches was determined by OD280. An aliquot of the suspension was centrifuged at 14,000 rpm, and the protein concentration in the supernatant was assessed.

Results:
Needle cluster like crystals were found in the following eight batches:
  acetate buffer pH 4.1 and sodium dihydrogen phosphate molarity of around 3.6 M to around 4.4 M (in 0.2 M steps),
  acetate buffer pH 4.6 and sodium dihydrogen phosphate molarity of around 4.0 M to around 4.4 M (in 0.2 M steps).

Crystal yield was assessed for the batches at acetate buffer pH 4.1 and sodium dihydrogen phosphate molarity of around 4.0 M to around 4.4 M. The crystal yield as determined by OD280 from residual protein concentration in the supernatant was above 95% after five days.

Precipitated species were obviously present in these batches immediately after combining the protein solution and the crystallization solution (milky suspension, typical light microscopic picture). As no precipitated species were observed after five days, it was concluded that formerly precipitated species rearranged into crystalline species. The protein is highly supersaturated in the crystallization mixture, and protein precipitates immediately. Some protein may still be dissolved, now either only slightly supersaturated or perhaps even below saturation. Crystals form, thereby further lowering the concentration of dissolved protein. Furthermore, the precipitated species clearly redissolve over time and are incorporated into the growing crystals.

Example 37

Sodium Dihydrogen Phosphate/Sodium Acetate Grid Screen Batch Crystallization at 1 mL Batch Volume, Different Protein Concentration D2E7 was used without exchanging the buffer (see Example 35).

D2E7 was brought to a concentration of around 10 mg/mL by diluting the liquid with Milli Q water.

Batch crystallization was performed by admixing around 500 µL of the protein solution with an equal amount of crystallization solution in well of a 24 well plate. 500 µL of a particular crystallization solution was prepared by admixing acetate buffer, sodium dihydrogen phosphate stock solution, potassium dihydrogen phosphate stock solution and Milli Q water in a well. In this example, the acetate buffer molarity was 0.1 M, and the acetate buffer pH was around 4.1 or 4.6. Sodium dihydrogen phosphate molarity was varied from around 2.6 M sodium dihydrogen phosphate to around 4.4 M sodium dihydrogen phosphate in 0.2 M steps. The wells were subsequently sealed after preparation of the crystallization mixture to prevent water evaporation. Microscopy of the plate was performed multiple times during the following week. Furthermore, the crystal yield of one particular batch was determined by OD280. An aliquot of the suspension was centrifuged at 14,000 rpm, and the protein concentration in the supernatant was assessed.

Results:
Needle cluster-like crystals were found in the following six batches:
  acetate buffer pH 4.1 and sodium dihydrogen phosphate molarity of around 3.4 M to around 4.4 M (in 0.2 M steps).

Crystal yield was assessed for the batch at acetate buffer pH 4.1 and sodium dihydrogen phosphate molarity of around 4.2 M. The crystal yield as determined by OD280 from residual protein concentration in the supernatant was above 95% after eight days.

Precipitated species were obviously present in these batches immediately after combining the protein solution and the crystallization solution (milky suspension, typical light microscopic picture). As no precipitated species were observed after six days, it was concluded that a phase transition occurred where formerly precipitated species rearranged into crystalline species.

Example 38

Sodium Dihydrogen Phosphate/Sodium Acetate Batch Crystallization at 2 mL Batch Volume D2E7 was buffered into a 20 mM HEPES/150 mM sodium chloride buffer at pH 7.4. The protein concentration was adjusted to 10 mg/mL.

Batch crystallization was performed by admixing around 1 mL of the protein solution with an equal amount of crystallization solution in a 2 mL Eppendorf reaction tube. 1 mL of a particular crystallization solution was prepared by admixing acetate buffer, sodium dihydrogen phosphate stock solution and Milli Q water. In this example, the acetate buffer molarity was 0.1 M, and the acetate buffer pH was around 4.1. Sodium dihydrogen phosphate molarity was around 4.0 M, 4.2 M or 4.4 M. The reaction tubes were stored at ambient temperature. Microscopy of 1 µL aliquots was performed multiple times during the following week.

Results:
Needle cluster-like crystals were found in all batches after six days.

Precipitated species were obviously present in these batches immediately after combining the protein solution and the crystallization solution (milky suspension, typical light microscopic picture). Formerly precipitated species rearranged into crystalline species as described in Example 36.

Example 39

Sodium Dihydrogen Phosphate/Sodium Acetate Grid Screen Batch Crystallization at 1 mL Batch Volume, Different Protein Concentration D2E7 was used without exchanging the buffer (see Example 35).

Batch crystallization was performed by admixing around 500 µL of the protein solution with an equal amount of crystallization solution in well of a 24 well plate. 500 µL of a particular crystallization solution was prepared by admixing acetate buffer, sodium dihydrogen phosphate stock solution, potassium dihydrogen phosphate stock solution and Milli Q water in a well. In this example, the acetate buffer molarity was 0.1 M, and the acetate buffer pH was around 4.1. Sodium dihydrogen phosphate molarity was varied from around 0.2 M to around 4.4 M in 0.2 M steps. The wells were subsequently sealed after preparation of the crystallization mixture to prevent water evaporation. Microscopy of the plate was performed multiple times during the following week. Furthermore, the crystal yield of the batch was determined by OD280. An aliquot of the suspension was centrifuged at 14,000 rpm, and the protein concentration in the supernatant was assessed.

Results:
Needle cluster-like crystals were found in the following two batches:
  sodium dihydrogen phosphate molarity of around 3.4 M and around 3.6 M.

Precipitated species and oily precipitation phases were also present in these crystal containing batches Example 40

Sodium Dihydrogen Phosphate/Sodium Acetate Batch Crystallization at 20 mL Batch Volume, Agitation D2E7 was used without exchanging the buffer (see Example 35).

D2E7 was brought to a concentration of around 10 mg/mL by dilution with Milli Q water.

Batch crystallization was performed by admixing around 10 mL of protein solution with an equal amount of crystallization solution in a 50 mL Falcon tube. 10 mL of the crystallization solution was prepared by admixing acetate buffer, sodium dihydrogen phosphate stock solution and Milli Q water in the tube. In this example, the acetate buffer molarity was 0.1 M, and the acetate buffer pH was around 4.1. Sodium dihydrogen phosphate molarity was 4.2 M. The tube was stored at ambient temperature, agitating the batch on a laboratory shaker. Microscopy of a 1 µL aliquot of the solution was performed multiple times during the following month.

Results:

Precipitated matter was observed in this batch.

Example 41a

Sodium Dihydrogen Phosphate/Sodium Acetate Batch Crystallization at 100 mL Batch Volume, No Agitation D2E7 was used without exchanging the buffer (see Example 35).

D2E7 was brought to a concentration of around 10 mg/mL by dilution with Milli Q water.

Batch crystallization was performed by admixing around 50 mL of protein solution with an equal amount of crystallization solution in a clean 1 L polypropylene bottle. 50 mL of the crystallization solution was prepared by admixing acetate buffer, sodium dihydrogen phosphate stock solution and Milli Q water in the tube. In this example, the acetate buffer molarity was 0.1 M, and the acetate buffer pH was around 4.1. Sodium dihydrogen phosphate molarity was 4.2 M. The container was stored at ambient temperature. Microscopy of a 1 µL aliquot of the solution was performed multiple times during the following month.

Results:

Needle cluster like crystals were observed after seven days. The crystal yield as determined by OD280 from residual protein concentration in the supernatant was above 95% after seven days.

Precipitated species were present in this batch immediately after combining the protein solution and the crystallization solution (milky suspension, typical light microscopic picture). Since no precipitated species were observed after seven days, it was concluded that a phase transition occurred where formerly precipitated species rearranged into crystalline species.

Example 41b

Sodium Dihydrogen Phosphate/Sodium Acetate Batch Crystallization at 1 mL, 50 mL and 10 L Batch Volume, No Agitation Large-scale crystallization of D2E7 was also performed by combining 1 L of 50 mg/mL D2E7 in Adalimumab commercial buffer formulation pH 5.2 (see Example 35) and 4 L water for injection (WFI) in a 10 L polypropylene vessel (Nalgene®). The solution was homogenized by gentle shaking. This 5 L D2E7 solution (10 mg/mL) was then mixed with 5 L of precipitating agent solution (5 M sodium dihydrogen phosphate, 4,400 mL, 1 M sodium acetate buffer, pH 4.1, 500 mL, WFI (Ampuwa), 100 mL) The precipitating agent solution was added in 500 mL portions. After addition of each portion the solution was homogenized by gently rotating/inverting the bottle. After addition of around 2,500 to –3,000 mL of the precipitating agent solution, a white precipitate appeared. The remaining precipitating agent was added all at once. Then the crystal preparation was homogenized (gently rotating/inverting) again.

Immediately after batch manufacture (i.e. after admixing of 5 L D2E7 solution and 5 L precipitating agent), 1 mL (filled into low volume Eppendorf sample vials) and 50 mL aliquots (filled into 50 mL Falcon sample tubes) were pulled and stored adjacent to the vessel for control and for evaluation of the impact of batch size on D2E7 crystallization. As outlined by FIGS. 2 to 4, the batch volume (i.e. 1 mL, 50 mL and 10 L, respectively) had no impact on D2E7 crystal needle/needle cluster size.

Discussion of Results of Batch Crystallization Experiments:

As the applied micro scale technique (see Section D. supra) is not feasible for large scale production of protein crystals, the crystallization conditions discovered by these micro scale methods were transferred into a scaleable batch mode.

D2E7 was successfully crystallized at 100 mL batch volume with ultimately high yield (>95%) and reproducibility, indicating that this crystallization system is applicable for industrial processing. By SDS-PAGE analysis, the protein character of the crystals was proven. SE-HPLC analysis of redissolved crystals showed only a slight increase in aggregated species. Washing of the crystals was possible by using an acetate buffer containing sodium dihydrogen phosphate around 4.2M sodium dihydrogen phosphate in around 0.1M sodium acetate at a pH around 4.1. No measurable solubility of D2E7 crystals in such a washing buffer occurs, as analyzed by OD280, recovering more than 90% of the crystals.

The experimental conditions of the above batch experiments are summarized in the following Table 1:

TABLE 1

| | | Batch Experiments | | | | | | | |
|---|---|---|---|---|---|---|---|---|---|
| Ex. | Batch Volume | Crystallization solution | Buffer Exchange | Yield Crystals | pH Buffer | pH Final | Final Protein Conc. mg/ml | Temp. | day of visual control |
| 33 | 800 µl | 0.1M NaAc, NaH2PO4 0.9M, KH2PO4 0.9M | yes | none | 4.1 | | 2.5-10 | amb | 11 d |
| 34 | 600 µl | 0.1M NaAc, NaH2PO4 1.5-2.4M | yes | none | 4.1 | | 5 | amb | 11 d |
| 35 | 1 ml | 0.1M NaAc, NaH2PO4 0.7M, KH2PO4 0.7M | | none | 4.1-5.6 | | 5 | amb | 4 d |

TABLE 1-continued

Batch Experiments

| Ex. | Batch Volume | Crystallization solution | Buffer Exchange | Yield Crystals | pH Buffer | pH Final | Final Protein Conc. mg/ml | Temp. | day of visual control |
|---|---|---|---|---|---|---|---|---|---|
|  |  | 0.1M NaAc, NaH2PO4 0.9M, KH2PO4 0.9M |  |  | 4.1-5.6 |  |  |  |  |
|  |  | 0.1M NaAc, NaH2PO4 1.8M, |  |  | 4.1-5.6 |  |  |  |  |
|  |  | 0.1M NaAc, NaH2PO4 2.1M, |  |  | 4.1-5.6 |  |  |  |  |
|  |  | 0.1M NaAc, NaH2PO4 2.4M, |  |  | 4.1-5.6 |  |  |  |  |
| 36 | 1 ml | 0.1M NaAc, NaH2PO4 3.6-4.4M | yes | >95% | 4.1 | 3.9-3.7 | 5 | amb | 5 d |
|  |  | 0.1M NaAc, NaH2PO4 4.0-4.4M |  |  | 4.6 | 4.0-3.9 |  | amb |  |
| 37 | 1 ml | 0.1M NaAc, NaH2PO4 3.4-4.4M |  | >95% | 4.1 | 3.9-3.7 | 5 | amb | 6 d |
| 38 | 2 ml | 0.1M NaAc, NaH2PO4 4.0-4.4M | yes | n.d. | 4.1 | 3.9-3.7 | 5 | amb | 6 d |
| 39 | 1 ml | 0.1M NaAc, NaH2PO4 3.4-3.6M |  | n.d + precipitate | 4.1 |  | 25 | amb | 6 d |
| 40 | 20 ml with agitation | 0.1M NaAc, NaH2PO4 4.2M |  | precipitate | 4.1 | 3.8 | 5 | amb | 4 d |
| 41a | 100 ml no agitation | 0.1M NaAc, NaH2PO4 4.2M |  | >95% | 4.1 | 3.8 | 5 | amb | 7 d |
| 41b | 1 ml, 50 ml or 10 l | 0.1M NaAc, NaH2PO4 4.4M |  | n.d. | 4.1 | n.d. | 5 | amb |  |

E. Methods for Crystal Processing and Analysis

Example 42

Washing of Crystals

After formation of the crystals, a washing step without redissolving the crystals is favourable. Therefore, after the crystallization process was finished, the crystal slurry was transferred into a centrifugation tube and centrifuged at 500 to 1000×g for twenty minutes. The centrifugation was performed at 4° C., but might also be performed at other feasible temperatures, e.g. room temperature. After centrifugation, the supernatant was discarded, and the crystal pellet was resuspended in a buffer containing around 4.2 M sodium dihydrogen phosphate in around 0.1 M sodium acetate at a pH around 4.1. No measurable solubility of D2E7 crystals in the washing buffer occurred, as analyzed by OD280. The centrifugation/resuspension steps were subsequently repeated for one to three times, and after this washing procedure, the pellet was resuspended and stored in a buffer containing around 4.2 M sodium dihydrogen phosphate in around 0.1 M sodium acetate at a pH around 4.1.

Example 43

Analysis of Crystals by SDS-PAGE

To prove the protein character of the crystals, the crystals were washed with a washing buffer as described in example 42. After assuring by OD280 that no more dissolved protein was present in the supernatant after centrifugation, the supernatant was discarded, and the crystals were subsequently dissolved in distilled water. OD280 measurement of this solution revealed that the crystals essentially consisted of protein, as the absorbance of the sample was now significantly higher as in the residual washing buffer. SDS-PAGE analysis of this solution of redissolved crystals, when compared to an original D2E7 sample, showed the same pattern.

F. Miscellaneous Examples

Concentration values given in the following examples are initial values referring to the antibody solution and the crystallization solution before mixing of the two solutions.

All pH values, if not described otherwise, refer to the pH of an acetate buffer stock before it was combined with other substances, like the crystallization agent.

All buffer molarities, if not described otherwise, refer to sodium acetate concentrations in a stock solution before pH adjustment, typically performed using acetic acid glacial.

Example 44

Solid Crystallization Agent

D2E7 was used without exchanging the buffer (see Example 35).

D2E7 was brought to a concentration of around 10 mg/mL by diluting the liquid with Milli Q water.

Batch crystallization was performed by admixing around 500 µL of the protein solution with an equal amount of acetate buffer (0.1 M, pH 4.1 or 4.6, respectively) in a well of a 24 well plate. Subsequently, solid sodium dihydrogen phosphate dihydrate was added at six different ratios to each pH setting: around 0.23 g, 0.27 g, 0.30 g, 0.33 g, 0.36 g and 0.39 g. Thus, after complete dissolution of the crystallization agent, the concentration was around 1.5M to 2.5M in 0.2M steps. The wells were subsequently sealed and the plate was agitated on a laboratory shaker until complete dissolution of the crystallization agent. Thereafter, the 24 well plate was stored at ambient temperature without agitation. Microscopy of the plate was performed after five days.

Results:

Needle cluster-like crystals were found in the following seven batches:
  acetate buffer pH 4.1 and sodium dihydrogen phosphate molarity of around 2.1 M, 2.3M and 2.5M, respectively.
  acetate buffer pH 4.6 and sodium dihydrogen phosphate molarity of around 1.9M, 2.1 M, 2.3M and 2.5M, respectively.

Example 45

Different Buffer Preparation Protocol and Preparation of Crystals

In this example, the acetate buffers were prepared as described in the following: 3 g of acetic acid glacial were diluted with around 42 mL of purified water. The pH was adjusted with sodium hydroxide solution and the volume adjusted to 50 mL. In this case, the total acetate amount is fixed at 1M (100 mM in the crystallization solution, or 50 mM in the crystallization mixture) and not expanded by pH adjustment.

D2E7 was used without exchanging the buffer (see Example 35).

D2E7 was brought to a concentration of around 10 mg/mL by diluting the liquid with Milli Q water.

Batch crystallization was performed by admixing around 500 μL of the protein solution with an equal amount of crystallization solution in well of a 24 well plate. 500 μL of a particular crystallization solution was prepared by admixing acetate buffer, sodium dihydrogen phosphate stock solution, potassium dihydrogen phosphate stock solution and Milli Q water in a well. In this example, the acetate buffer molarity was 0.1 M, and the acetate buffer pH was around 4.1 and 4.6, respectively. Sodium dihydrogen phosphate molarity was varied from around 3.4 M to around 4.4 M in 0.2 M steps. The wells were subsequently sealed after preparation of the crystallization mixture to prevent water evaporation. Microscopy of the plate was performed after five days.

Results:

Needle cluster-like crystals were found in the following nine batches:
- acetate buffer pH 4.1 and sodium dihydrogen phosphate molarity of around 3.6 to 4.4, in 0.2 steps.
- acetate buffer pH 4.6 and sodium dihydrogen phosphate molarity of around 3.6 to 4.2, in 0.2 steps.

Example 46

Preparation of Encapsulated Crystals

Crystals as obtained in example 41 are positively charged as determined via zeta potential measurement using a Malvern Instruments Zetasizer nano.

The crystals are washed and suspended in a buffer containing excipients which conserve crystallinity, and which has a pH that keeps the crystals charged. Subsequently, an appropriate encapsulating agent is added to the crystal suspension. In this context, an appropriate encapsulating agent is a (polymeric) substance with low toxicity, biodegradability and counter ionic character. Due to this counter ionic character, the substance is attracted to the crystals and allows coating. By this technique, the dissolution of crystals in media which do not contain any other excipient maintaining crystallinity is preferably sustained.

Example 47

Preparation of Encapsulated/Embedded Crystals

Crystals are obtained as described in example 41.

The crystals are washed and suspended in a buffer containing excipients which conserve crystallinity.

The crystals can then be
- embedded by drying the crystals and combining these dried crystals with a carrier, e.g. by compression, melt dispersion, etc.
- encapsulated/embedded by combining a crystal suspension with a carrier solution which is not miscible with water. The carrier precipitates after removal of the solvent of the carrier. Subsequently, the material is dried.
- encapsulated/embedded by combining a crystal suspension with a water miscible carrier solution. The carrier precipitates as its solubility limit is exceeded in the mixture.
- embedded by combining dried crystals or a crystal suspension with a water miscible carrier solution.
- embedded by combining dried crystals with a carrier solution which is not water miscible.

G. Crystal Characterization

In the following section experiments that were performed to determine whether crystalline monoclonal antibody D2E7 retains the bioactivity characteristic of never-crystallized D2E7 upon redissolution of the crystalline material are summarized.

G1. Bioactivity Test with Murine L-929 Cells a) General Method

The neutralizing effect of D2E7 solution against the cytotoxic effect of recombinant human TNF (rHuTNF) was determined. This involved incubating mouse L-929 cells as indicator in a 96-well microtiter plate in the presence of various D2E7 concentrations for 48 hours with a defined amount of rHuTNF at 37° C. The surviving cells were stained with crystal violet. The intensity of color was measured by spectrophotometry in the individual wells of the microtiter plate and evaluated. The $IC_{50}$ was measured, i.e. the concentration of D2E7 which reduced the cytotoxic effect of rHuTNF on L-929 cells such that 50% of the cells survived.

In a separate dilution box, starting from the 1 μg protein/mL dilutions, the 9 titer curve measuring points (curve dilutions) were prepared individually in the dilution tubes for sample and reference standard.

The L-929 cell suspension to be used was diluted with medium to provide a concentration of 60,000 cells/mL. Subsequently 100 μL per well of the respective cell concentration were pipetted into columns 1-11 of the test plate. The wells in column 12 contained only 100 μL of medium each. Incubation was applied at 37° C. and 5% (v/v) $CO_2$ for 24 hours in the test plate.

After 24 hours' incubation, 50 μL of each of the 9 titer curve dilutions were transferred from the dilution box to the test plate for the reference standard or sample, i.e. for the reference standard to wells in rows A-D in columns 1-9 and for the sample to the wells in rows E-H in columns 1 to 9.

50 μL of medium were pipetted into column 10; and 100 μL each were pipetted into columns 11 and 12.

50 μL of TNF reference standard (12.5 ng protein/mL medium) were pipetted into the wells in column 1 to 10, row A to H, whereby column 10 corresponded to the 100% lysis value (TNF control).

Column 11 was a 100% growth control, and column 12 contained no cell material and thus acted as a blank. The final volume per well was 200 μL.

Incubation of the test plates was performed for 48 hours at 37° C. and with 5% $CO_2$. Following incubation for 2 days, the liquids from the test plate wells were discarded by turning quickly and giving a single, vigorous downward shake. Then 50 μL of crystal violet solution (0.75% crystal violet, 0.35% sodium chloride, 32.4% ethanol and 8.6% formaldehyde) were pipetted into each well. The solution was left in the wells for 15 minutes and then discarded as described above. Then the plates were washed and dried at room temperature for about 30 minutes. Subsequently, 100 μL of reagent solution (50% ethanol and 0.1% acetic acid) were pipetted into each well. Agitation of the plates (at about 300 rpm for 15 min) produced an evenly colored solution in each of the wells.

The absorbance of the dye in the test plate wells was measured in a plate photometer at 620 nm. Individual values were plotted on a graph, with the absorbance (y axis) being plotted against the respective dilution or concentration ng/mL (x axis) of antibody. From the 4-parameter plot, the concentration was read off at which half the cells survive and half die (IC$_{50}$ value). This concentration was calculated by parameter 3 of the 4-parameter function of the curve data. The mean values of the reference standard concentrations were calculated. The relative biological activity of the sample was calculated by dividing the mean IC$_{50}$ value of the reference standard by the individual IC$_{50}$ values of the sample and multiplication by 100%. The relative activities were then averaged.

b) Relative Activity for D2E7 Crystals

The test was performed as a comparison of the biological activity of the sample to that of a reference standard. The absorption values, plotted versus the concentration of D2E7 and assessed by a 4-parameter nonlinear regression, revealed the IC$_{50}$ values for the inhibition of the TNF effect by the antibody. Since both samples were run in four repeats on one microplate this results in four IC$_{50}$ values for D2E7 reference standard and sample respectively. Subsequently, the mean of the IC$_{50}$ values of the reference standard was calculated and the relative activity of each repeat of the sample was assessed by dividing the mean IC$_{50}$ value of the reference standard by the relevant IC$_{50}$ value of the sample and multiplication by 100%.

The test of the sample (crystal suspension 2.7 mg/mL, prepared as described in Example 36) revealed a relative biological activity of 111%.

Thus, the sample can be considered as fully biologically active.

G2. Microscopic Characterization

In the following, data on microscopic characterization of crystals of D2E7 will be presented.

a) Optical Analysis of mAb Crystal Batch Samples

After homogenization, aliquots of 1 to 10 µL sample volume were pipetted onto an object holder plate and were covered with a glass cover slide. The crystal preparations were assessed using a Zeiss Axiovert 25 inverted light microscope equipped with E-PI 10× oculars and 10×, 20× and 40× objectives, respectively. Pictures were taken using a digital camera (Sony Cybershot DSC S75).

b) Optical Analysis of Vapor Diffusion Experiments, Assessment of Approximate Crystal Sizes and Detection of Birefringence For this purpose, a Nikon Labophot microscope was used, equipped with CFW 10× oculars and 4×, 10×, 20× and 40× objectives, respectively.

For assessment of vapor diffusion experiments, the sample drops in the 24 well plates were screened.

Crystal sizes were assessed by transferring the microscopic picture onto a computer screen by means of a JVC TK C1380 color video camera, and by measuring the length or diameter of representative needle-like or needle cluster-like crystals, applying the JVC Digital Screen Measurement Comet software version 3.52a. Furthermore, the microscope was equipped with a filter set (polarizer and analyzer) to assess the birefringent behaviour of samples.

If the polarization directions of the polarizer and analyzer filters are set at a 90° angle relative to each other ("crossed polarizers"), no light will pass through to the microscope eyepiece; the image will appear dark or black. If now a sample, which is placed into the light beam between the crossed polarizers, is capable of rotating the polarization plane of the light, a distinct glimmering of the sample against a dark background will be observed. This behaviour, termed "birefringence", distinguishes ordered crystalline (anisotropic) from unordered amorphous (isotropic) matter. As birefringence is characteristic for anisotropic matter, this glimmering appearance proves the existence of crystalline matter. However, the absence of birefringence does not exclude the existence of crystalline matter, as the crystals might also exhibit cubic symmetry and therefore be isotropic, like amorphous matter.

c) Results

In the attached FIGS. 1 to 4 representative pictures of D2E7 crystals are presented.

FIG. 1 shows D2E7 crystals obtained by small-scale batch crystallization according to Example 37 after 6 days at room temperature (5 mg/ml final protein concentration; Crystallization buffer: 4.2 M sodium dihydrogen phosphate in 0.1 M sodium acetate, pH 4.1). The crystals exhibited birefringence.

Figure 2:
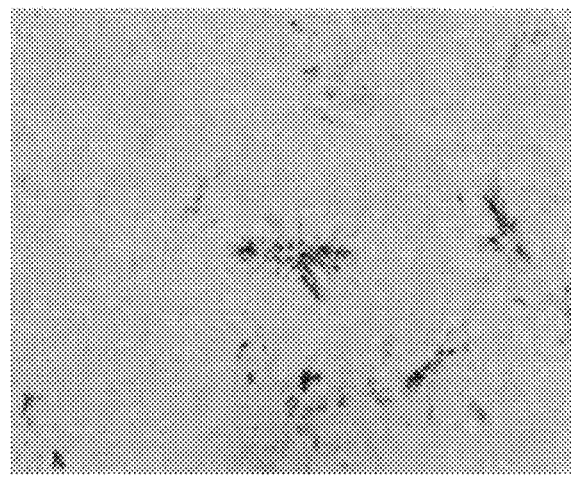
FIG. 2: D2E7 crystals manufactured in 1 mL batch volume, ambient temperature.
Figure 3:
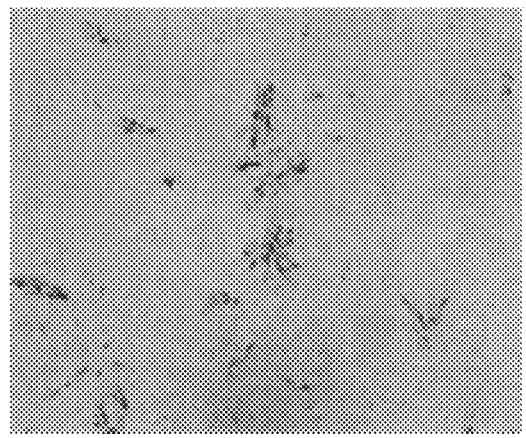
FIG. 3: D2E7 crystals manufactured in 50 mL batch volume, ambient temperature.
Figure 4:
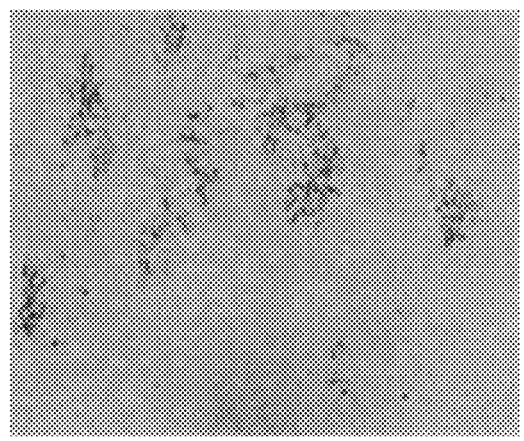
FIG. 4: D2E7 crystals manufactured in 10 L batch volume, ambient temperature.

FIGS. 2 to 4 show D2E7 crystals obtained by large-scale batch crystallization according to Example 41b.

Syringeability: A D2E7 crystal suspension 200 mg/mL protein incorporated in crystals and formulated in a buffer containing 20% (m/v) PEG 4,000 is syringeable through a 27½ G needle.

G3. Birefringence

In order to demonstrate that Adalimumab crystallization in fact provides crystalline material its birefringence was analyzed.

Protein: Diluted 70 mg/ml Adalimumab in formulation buffer with double-distilled water to 10 mg/ml.

Precipitant: 4 M NaH$_2$PO$_4$ (dissolved powder in double-distilled water)

Method: Micro batch crystallization in a hanging-drop tray with 2 ml compartment well, Mixed 500 µl protein solution with 500 µl protein; no NaOAc in the solution.

Temperature: 24° C.

Technical Equipment for birefringence measurement: Nikon SMZ1500 stereo dissecting microscope equipped with a Nikon CoolPix CCD camera. Crystal birefringence was photographed under crossed polarizers. Magnification is approximately 200×.

Figure 5A:
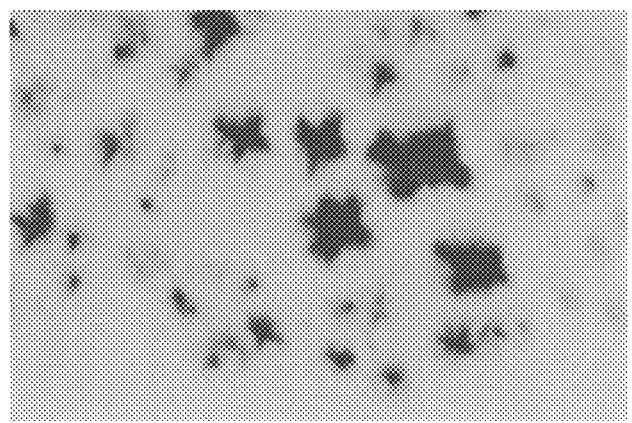
FIG. 5A shows clusters of Adalimumab needle-like crystals and was photographed under crossed polarizers.

Corresponding micrographs are shown in FIG. 5A. A marked birefringence of the clusters of Adalimumab needle-like crystals is observed. The colour of the crystals changes from blue to red, then back to blue, as the orientation of the crystal needle axis rotates relative to the light polarization direction.

Figure 5B:
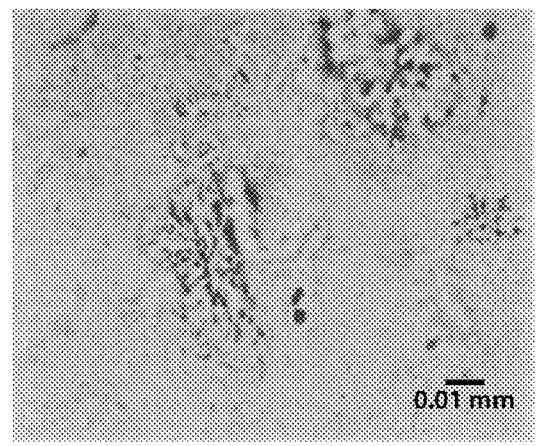
FIG. 5B is taken with plane polars and shows the particle morphology.

A further set of micrographs is depicted in FIGS. 5B, C and D.

All images were taken with a Nikon Eclipse E600 POL microscope and a Nikon DXM 1200 digital camera. Magnification is approximately 40×.

Figure 5C:
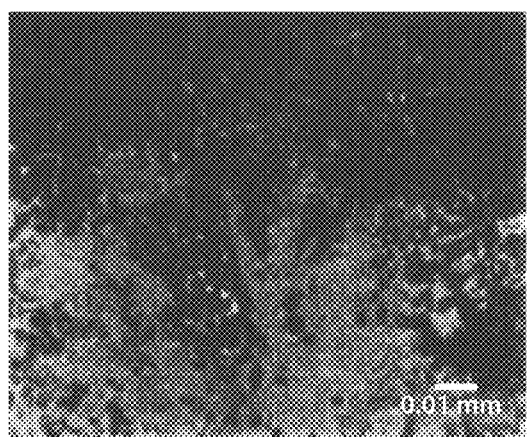
FIG. 5C shows birefringence and was taken with crossed polar and a red compensator or quarter wave plate.
Figure 5D:
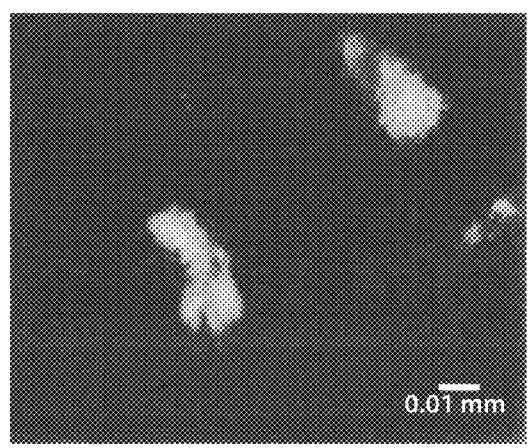
FIG. 5D shows birefringence and was taken with crossed polars.

The image of FIG. 5B (grey) is taken with plane polars and shows the particle morphology. The white crystals on the black background (FIG. 5D) show birefringence and were taken with crossed polars. The blue and orange crystals on the purple background (FIG. 5C) show birefringence and were taken with crossed polar and a red compensator or quarter wave plate.

H. Crystal Syringeability

In the following section, experiments were performed to determine the syringeability of crystalline suspensions (in PEG) of monoclonal antibody D2E7 (10-200 mg/ml) using different gauge needles.

PEG Buffer:
20% PEG 4,000 m/v
12 mg/mL mannitol
0.1 mg/mL polysorbate 80
1.305 mg/mL citric acid monohydrate
0.305 mg/mL sodium citrate
1.53 mg/mL di sodium hydrogen phosphate dehydrate 0.86 mg/mL sodium di hydrogen phosphate dehydrate
pH was adjusted to 5.2 with sodium hydroxide Syringe depletion (1 mL filling volume) was performed as it would be manually by a patient in the course of administration. 20-27.5 G needle sizes were evaluated.

Figure 6:
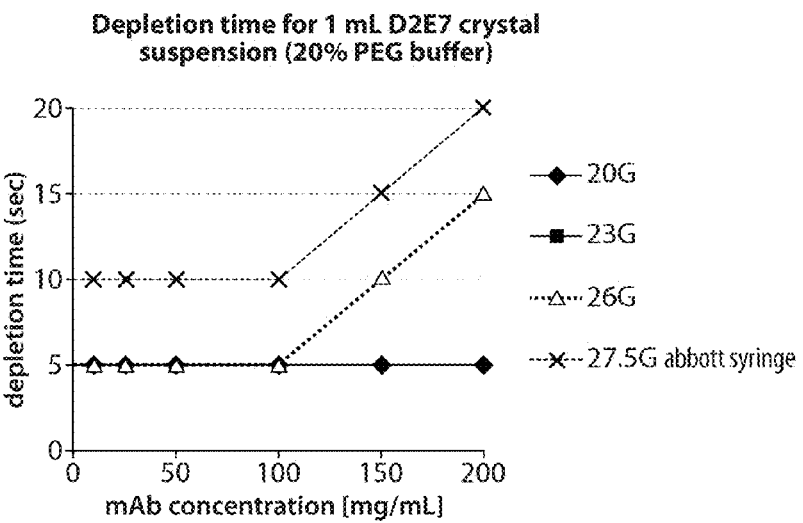
FIG. 6: D2E7 crystal suspensions at different concentrations injected via different gauge needles.

Syringes:
20/23/26 G:
Henke Sass Wolf GmbH 1 mL Norm-Ject syringes, equipped with
Henke Sass Wolf GmbH Fine-Ject® 20 G needles
Terumo® 23 G needles
Neopoint® 26 G needles
27.5 G:
BD HyPak SCF™ 1 mL long syringes, equipped with 27.5 G RNS needles 38800 Le Pont du Claix The results (FIG. 6) suggest that higher gauge needles provide a slower delivery of the crystals at high concentrations.

I. Stability Data (SE HPLC, FT-IR)

In the following section, experiments were performed to determine the stability of crystalline suspensions of monoclonal antibody D2E7 (50 and 200 mg/ml) over 12 month storage at 2-8° C.

Crystals suspended in medium as used in syringeability studies:
20% PEG 4,000 m/v
12 mg/mL mannitol
0.1 mg/mL polysorbate 80
1.305 mg/mL citric acid monohydrate
0.305 mg/mL sodium citrate
1.53 mg/mL di sodium hydrogen phosphate dehydrate
0.86 mg/mL sodium di hydrogen phosphate dehydrate
pH was adjusted to 5.2 with sodium hydroxide
SE-HPLC
50 mg/mL Adalimumab crystal suspension, stable at 2-8° C. over time

| Time point | Aggregates (%) | Monomer (%) | Fragments (%) |
|---|---|---|---|
| T0 | 1.3 | 98.5 | 0.2 |
| 1 month | 1.4 | 98.3 | 0.3 |
| 3 month | 2.2 | 97.5 | 0.3 |
| 6 month | 3.2 | 96.3 | 0.5 |
| 9 month | 4.0 | 95.5 | 0.5 |
| 12 month | 4.2 | 95.1 | 0.7 |

200 mg/mL Adalimumab

| Time point | Aggregates (%) | Monomer (%) | Fragments (%) |
|---|---|---|---|
| T0 | 1.3 | 98.5 | 0.2 |
| 1 month | 1.3 | 98.4 | 0.3 |
| 3 month | 1.9 | 97.8 | 0.3 |
| 6 month | 2.4 | 97.2 | 0.4 |
| 9 month | 2.5 | 97.0 | 0.5 |
| 12 month | 2.6 | 96.8 | 0.6 |

A Dionex HPLC system (P680 pump, ASI 100 autosampler, UVD170U) was used for stability analysis by SEC. D2E7 samples were separated on a GE Superose® 6 column, applying a flow rate of 0.5 mL/min. UV quantitation (detection) was performed at a wavelength of 214 nm. The running buffer consisted of 0.15M sodium chloride in 0.02M sodium phosphate buffer pH 7.5. IR spectra were recorded with a Confocheck system on a Bruker Optics Tensor 27. Liquid samples were analyzed using a MicroBiolytics AquaSpec cell. Each sample was assessed performing at least two measurements of 120 to 500 scans at 25° C. Blank buffer spectra were subtracted from the protein spectra, respectively. Protein second derivative spectra were generated by Fourier transformation and vector normalized from 1580-1720 cm$^{-1}$ for relative comparison. Redissolution of crystals was performed as follows: Crystal suspensions were diluted with Humira® commercial buffer to 10 mg/mL protein concentration. By decreasing PEG concentration crystals redissolved.

Figure 7:
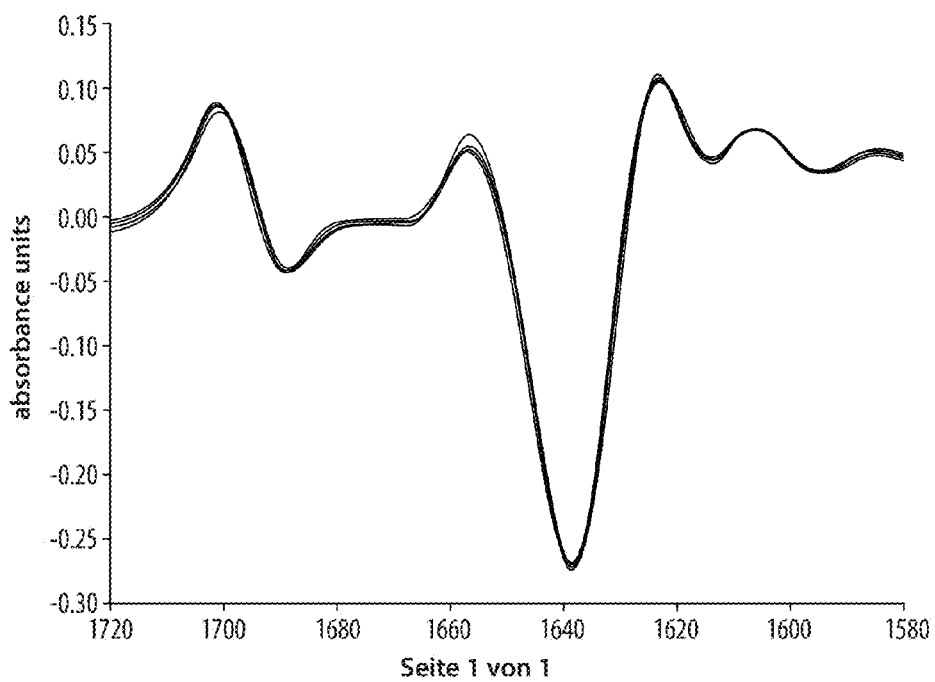
FIG. 7: FT-IR analysis of D2E7 crystal suspension.

Blue—standard, Humira® after freeze/thaw
Red—redissolved crystals after 6 month storage at 25° C., 50 mg/mL
Green—redissolved crystals after 6 month storage at 25° C., 200 mg/mL
Results:
FIG. 7 illustrates that there were no conformational differences over 6 months of storage at 25° C.

J. Morphology

After 12 months of storage at 2-8° C. no significant morphological changes were observed by light microscopy analysis of the crystals.

Aliquots of 1 to 10 µL sample volume were pipetted onto an object holder plate, diluted with formulation buffer (20% PEG) and covered with a glass cover slide. The preparations were assessed using a Zeiss Axiovert 25 inverted light microscope equipped with E-PI 10× oculars and 10×, 20× and 40× objectives, respectively.

REFERENCES

Baldock Peter; Mills, Vaughan; Stewart, Patrick Shaw, Journal of Crystal Growth (1996), 168(1-4, Crystallization of Biological Macromolecules), 170-174.
Connell, G. E., M. H. Freedman, et al. (1973). "Human IgG myeloma protein crystallizing with rhombohedral symmetry." *Canadian Journal of Biochemistry* 51(8): 1137-41.
Harris, L. J., S. B. Larson, et al. (1992). "The three-dimensional structure of an intact monoclonal antibody for canine lymphoma." *Nature (London, United Kingdom)* 360(6402): 369-72.
Huber, R., J. Deisenhofer, et al. (1976). "Crystallographic structure studies of an IgG molecule and an Fc fragment." *Nature* 264(5585): 415-20.
Jen, A., Merkle, H. P. (2001), Diamonds in the rough: Protein Crystals from a from a formulation perspective, *Pharm. Res.* (2001), 18, 11, 1483
Jentoft, J. E., D. G. Dearborn, et al. (1982). "Characterization of a human cryoglobulin complex: a crystalline adduct of a monoclonal IgG and albumin." *Biochemistry* 21(2): 289-294.
Jones, H. B. (1848). "On a new substance occurring in the urine of a patient with mollities ossium." *Philosophical Transactions of the Royal Society, London* 138: 55-62.
McPherson, A. (1999). *Crystallization of Biological Macromolecules*. Cold Spring Harbor, New York, Cold Spring Harbor Laboratory Press.
Mills, L. E., L. R. Brettman, et al. (1983). "Crystallocryoglobulinemia resulting from human monoclonal antibodies to albumin." *Annals of internal medicine* 99(5): 601-4.
Nisonoff, A., S. Zappacosta, et al. (1968). "Properties of crystallized rabbit anti-pazobenzoate antibody." *Cold Spring Harbor Symposia on Quantitative Biology* 32: 89-93.

Putnam, F. W. (1955). "Abnormal human serum globulins." *Science (Washington, D.C., United States)* 122: 275-7.

Rajan, S. S., K. R. Ely, et al. (1983). "Three-dimensional structure of the Mcg IgG1 immunoglobulin." *Molecular Immunology* 20(7): 787-99.

Sarma, V. R., E. W. Silverton, et al. (1971). "Three-dimensional structure at 6 Ang. Resolution of a human gG1 immunoglobulin molecule." *Journal of Biological Chemistry* 246(11): 3753-9.

Shenoy, B., C. P. Govardhan, et al. (2002). Pharmaceutical compositions comprising crystals of polymeric carrier-stabilized antibodies and fragments for therapeutic uses. PCT Int. Appl. WO, (Altus Biologics Inc., USA). 173 pp.

Terry, W. D., B. W. Matthews, et al. (1968). "Crystallographic studies of a human immunoglobulin." *Nature* 220(164): 239-41.

von Bonsdorf, B., H. Groth, et al. (1938). "On the Presence of a High-molecular Crystallizable Protein in Blood Serum in Myeloma." *Folia Haematologia* 59: 184-208.

Yang, M. X., B. Shenoy, et al. (2003). "Crystalline monoclonal antibodies for subcutaneous delivery." *Proceedings of the National Academy of Sciences of the United States of America* 100(12): 6934-6939.

---

The invention claimed is:

1. A method for treating a TNFalpha-related disorder in a subject in need thereof, said method comprising the step of administering to the subject an effective amount of anti-hTNFalpha antibody crystals,
wherein the antibody is an isolated human IgG antibody comprising two heavy chains each with a molecular weight of about 50 kpa, a light chain variable region (LCVR) comprising the amino acid sequence of SEQ ID NO: 1, and a heavy chain variable region (HCVR) comprising the amino acid sequence of SEQ ID NO: 2, and wherein the crystals have a needle-like morphology with a length 1 of about 2-500 μm and an 1/d ratio of about 3 to 30.

2. A method for treating a TNFalpha-related disorder in a subject in need thereof, said method comprising the step of administering to the subject an effective amount of a pharmaceutical composition comprising:
(a) crystals of an isolated human IgG anti-hTNFalpha antibody, wherein the antibody comprises two heavy chains each with a molecular weight of about 50 kpa, a light chain variable region (LCVR) comprising the amino acid sequence of SEQ ID NO: 1, and a heavy chain variable region (HCVR) comprising the amino acid sequence of SEQ ID NO: 2, and wherein the crystals have a needle-like morphology with a length 1 of about 2-500 μm and an 1/d ratio of about 3 to 30, and
(b) a pharmaceutical excipient.

3. The method according to claim 2, wherein the pharmaceutical composition is administered to the subject by parenteral route, oral route, or injection.

4. The method of claim 1 or 2, wherein said TNFalpha-related disorder is selected from the group consisting of an allergy, multiple sclerosis, autoimmune diabetes, autoimmune uveitis and nephrotic syndrome; an infectious disease, transplant rejection or graft-versus-host disease, malignancy, pulmonary disorder, cardiac disorder, inflammatory bone disorders, bone resorption disease, alcoholic hepatitis, viral hepatitis, fulminant hepatitis, coagulation disturbances, burns, reperfusion injury, keloid formation, scar tissue formation, pyrexia, periodontal disease, obesity and radiation toxicity; a pulmonary disorder, a coronary disorder, a metabolic disorder, anemia, pain, a hepatic disorder, a skin disorder, a nail disorder, or vasculitis, Behcet's disease, ankylosing spondylitis, asthma, chronic obstructive pulmonary disease (COPD), idiopathic pulmonary fibrosis (IPF), restenosis, diabetes, anemia, pain, a Crohn's disease-related disorder, a hepatitis C virus infection, age-related cachexia, Alzheimer's disease, brain edema, inflammatory brain injury, chronic fatigue syndrome, dermatomyositis, drug reactions, edema in and/or around the spinal cord, familial periodic fevers, Felty's syndrome, fibrosis, glomerulonephritides (e.g. post-streptococcal glomerulonephritis or IgA nephropathy), loosening of prostheses, microscopic polyangiitis, mixed connective tissue disorder, multiple myeloma, cancer and cachexia, multiple organ disorder, myelo dysplastic syndrome, orchitism osteolysis, pancreatitis, including acute, chronic, and pancreatic abscess, periodontal disease polymyositis, progressive renal failure, pseudogout, pyoderma gangrenosum, relapsing polychondritis, rheumatic heart disease, sarcoidosis, sclerosing cholangitis, stroke, thoracoabdominal aortic aneurysm repair (TAAA), TNF receptor associated periodic syndrome (TRAPS), symptoms related to Yellow Fever vaccination, an inflammatory disease associated with the ear, chronic ear inflammation, or pediatric ear inflammation, uveitis, sciatica, prostatitis, endometriosis, choroidal neovascularization, lupus, Sjogren's syndrome, and wet macular degeneration.

5. The method of claim 2, wherein the pharmaceutical excipient embeds or encapsulates the crystals.

6. The method of claim 1 or 2, wherein the IgG antibody is selected from the group consisting of an IgG1 antibody, an IgG2 antibody, an IgG3 antibody, and an IgG4 antibody.

7. The method of claim 1 or 2, wherein the antibody is an IgG1 antibody.

8. The method of claim 1 or 2, wherein the antibody is adalimumab.

9. The method of claim 2, wherein the composition has an antibody concentration greater than about 1 mg/ml.

10. The method of claim 2, wherein the composition has an antibody concentration greater than about 200 mg/ml.

11. The method of claim 1, wherein the crystal is combined with a polymeric carrier or an oil or lipid carrier.

12. The method of claim 11, wherein the polymeric carrier is a polymer selected from one or more of the group consisting of: poly(acrylic acid), poly(cyanoacrylates), poly(amino acids), poly(anhydrides), poly(depsipeptide), poly(esters), poly(lactic acid), poly(lactic-co-glycolic acid) or PLGA, poly(β-hydroxybutryate), poly(caprolactone), poly(dioxanone); poly(ethylene glycol), poly(hydroxypropyl)methacrylamide, poly[(organo) phosphazene, poly(ortho esters), poly(vinyl alcohol), poly(vinylpyrrolidone), maleic anhydride alkyl vinyl ether copolymers, pluronic polyols, albumin, alginate, cellulose and cellulose derivatives, collagen, fibrin, gelatin, hyaluronic acid, oligosaccharides, glycami-noglycans, sulfated polysaccharides, blends and copolymers thereof.

13. The method of claim 1 or 2, wherein said TNFalpha-related disorder is an autoimmune disease.

14. The method of claim 13, wherein the autoimmune disease is selected from the group consisting of rheumatoid arthritis, rheumatoid spondylitis, osteoarthritis and gouty arthritis.

15. The method of claim 1 or 2, wherein said TNFalpha-related disorder is an intestinal disorder.

16. The method of claim 1 or 2, wherein said TNFalpha-related disorder is a spondyloarthropathy.

17. The method of claim 1 or 2, wherein said TNFalpha-related disorder is rheumatoid arthritis.

18. The method of claim 1 or 2, wherein said TNFalpha-related disorder is psoriatic arthritis.

19. The method of claim 1 or 2, wherein said TNFalpha-related disorder is psoriasis.

20. The method of claim 19, wherein the psoriasis is chronic plaque psoriasis.

21. The method of claim 1 or 2, wherein said TNFalpha-related disorder is juvenile rheumatoid arthritis (JRA).

* * * * *

UNITED STATES PATENT AND TRADEMARK OFFICE
CERTIFICATE OF CORRECTION

PATENT NO.        : 8,772,458 B2                                          Page 1 of 1
APPLICATION NO.   : 13/774706
DATED             : July 8, 2014
INVENTOR(S)       : Koenigsdorfer et al.

It is certified that error appears in the above-identified patent and that said Letters Patent is hereby corrected as shown below:

In the Claims

Claim 1, column 55, line 38 replace "50 kpa" with --50kDa--.

Claim 2, column 55, line 51 replace "50 kpa" with --50kDa--.

Signed and Sealed this
Eleventh Day of November, 2014

Michelle K. Lee
*Deputy Director of the United States Patent and Trademark Office*

SEQUENCE LISTING

```
<160> NUMBER OF SEQ ID NOS: 6

<210> SEQ ID NO 1
<211> LENGTH: 107
<212> TYPE: PRT
<213> ORGANISM: Artificial
<220> FEATURE:
<223> OTHER INFORMATION: variable region of D2E7 light chain

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105

<210> SEQ ID NO 2
<211> LENGTH: 121
<212> TYPE: PRT
<213> ORGANISM: Artificial
<220> FEATURE:
<223> OTHER INFORMATION: variable region of D2E7 heavy chaim

<400> SEQUENCE: 2

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110
```

```
Gln Gly Thr Leu Val Thr Val Ser Ser
        115                 120

<210> SEQ ID NO 3
<211> LENGTH: 9
<212> TYPE: PRT
<213> ORGANISM: Artificial
<220> FEATURE:
<223> OTHER INFORMATION: D2E7 light chain CDR3 region
<220> FEATURE:
<221> NAME/KEY: MISC_FEATURE
<222> LOCATION: (9)..(9)
<223> OTHER INFORMATION: Xaa is Thr or Ala

<400> SEQUENCE: 3

Gln Arg Tyr Asn Arg Ala Pro Tyr Xaa
1               5

<210> SEQ ID NO 4
<211> LENGTH: 12
<212> TYPE: PRT
<213> ORGANISM: Artificial
<220> FEATURE:
<223> OTHER INFORMATION: D2E7 heavy chaim CDR3 region
<220> FEATURE:
<221> NAME/KEY: MISC_FEATURE
<222> LOCATION: (12)..(12)
<223> OTHER INFORMATION: Xaa is Tyr or Asn

<400> SEQUENCE: 4

Val Ser Tyr Leu Ser Thr Ala Ser Ser Leu Asp Xaa
1               5                   10

<210> SEQ ID NO 5
<211> LENGTH: 214
<212> TYPE: PRT
<213> ORGANISM: Artificial
<220> FEATURE:
<223> OTHER INFORMATION: D2E7 light chain sequence

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

-continued

```
                165                 170                 175
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 6
<211> LENGTH: 451
<212> TYPE: PRT
<213> ORGANISM: Artificial
<220> FEATURE:
<223> OTHER INFORMATION: D2E7 heavy chain sequence
<220> FEATURE:
<221> NAME/KEY: MISC_FEATURE
<222> LOCATION: (451)..(451)
<223> OTHER INFORMATION: Xaa is missing or is Lys

<400> SEQUENCE: 6

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285
```

```
His Asn Ala Lys Thr Lys Pro Arg Glu Glu Gln Tyr Asn Ser Thr Tyr
    290             295                 300

Arg Val Val Ser Val Leu Thr Val Leu His Gln Asp Trp Leu Asn Gly
305             310              315                 320

Lys Glu Tyr Lys Cys Lys Val Ser Asn Lys Ala Leu Pro Ala Pro Ile
                325             330                 335

Glu Lys Thr Ile Ser Lys Ala Lys Gly Gln Pro Arg Glu Pro Gln Val
                340             345             350

Tyr Thr Leu Pro Pro Ser Arg Asp Glu Leu Thr Lys Asn Gln Val Ser
            355             360                 365

Leu Thr Cys Leu Val Lys Gly Phe Tyr Pro Ser Asp Ile Ala Val Glu
    370             375                 380

Trp Glu Ser Asn Gly Gln Pro Glu Asn Asn Tyr Lys Thr Thr Pro Pro
385             390                 395                 400

Val Leu Asp Ser Asp Gly Ser Phe Phe Leu Tyr Ser Lys Leu Thr Val
                405             410                 415

Asp Lys Ser Arg Trp Gln Gln Gly Asn Val Phe Ser Cys Ser Val Met
            420             425                 430

His Glu Ala Leu His Asn His Tyr Thr Gln Lys Ser Leu Ser Leu Ser
            435             440                 445

Pro Gly Xaa
    450
```